United States Patent [19]

Schössler

[11] Patent Number: 4,600,797

[45] Date of Patent: Jul. 15, 1986

[54] PROCESS FOR THE PREPARATION OF NITROAMINOBENZENES

[75] Inventor: Willi Schössler, Cologne, Fed. Rep. of Germany

[73] Assignee: Bayer Aktiengesellschaft, Leverkusen, Fed. Rep. of Germany

[21] Appl. No.: 468,030

[22] Filed: Feb. 18, 1983

Related U.S. Application Data

[63] Continuation-in-part of Ser. No. 359,331, Mar. 18, 1982, abandoned, which is a continuation of Ser. No. 199,888, Oct. 23, 1980, abandoned, and a continuation-in-part of Ser. No. 199,889, Oct. 23, 1980, abandoned, and Ser. No. 199,876, Oct. 23, 1986, abandoned.

[30] Foreign Application Priority Data

Oct. 23, 1979 [DE] Fed. Rep. of Germany ....... 2942676
Sep. 9, 1980 [DE] Fed. Rep. of Germany ....... 3033862
Oct. 10, 1980 [DE] Fed. Rep. of Germany ....... 3038394

[51] Int. Cl.$^4$ .............................................. C07C 85/02
[52] U.S. Cl. ..................... 564/414; 564/99; 564/218; 564/223; 564/373; 564/411; 564/413; 564/441; 260/508; 260/509; 560/22; 560/250; 562/437
[58] Field of Search ............... 564/393, 411, 413, 414, 564/441, 218, 223, 99; 260/508, 509; 560/22, 250; 562/437

[56] References Cited

U.S. PATENT DOCUMENTS

| | | | |
|---|---|---|---|
| 1,314,923 | 4/1919 | Andrews | 564/414 |
| 1,400,555 | 12/1921 | Kasai | 564/414 |
| 1,963,598 | 6/1934 | Tinker et al. | 260/124 |
| 2,092,970 | 9/1937 | Herstein | 260/124 |
| 2,459,002 | 1/1949 | Parker et al. | 260/556 |
| 2,525,508 | 10/1950 | Zimmerman et al. | 260/575 |
| 2,686,810 | 8/1954 | Koch et al. | 260/578 |
| 3,117,911 | 1/1964 | Kalopissis et al. | 167/88 |
| 3,794,676 | 2/1974 | Halasz | 260/471 |

FOREIGN PATENT DOCUMENTS

| | | | |
|---|---|---|---|
| 767072 | 8/1951 | Fed. Rep. of Germany | 129/102 |
| 2226405 | 12/1973 | Fed. Rep. of Germany | . |
| 0027658 | 10/1980 | Fed. Rep. of Germany | . |
| 2942676 | 5/1981 | Fed. Rep. of Germany | . |
| 3033862 | 4/1982 | Fed. Rep. of Germany | . |
| 3038394 | 5/1982 | Fed. Rep. of Germany | . |
| 469080 | 7/1937 | United Kingdom | . |
| 1434098 | 4/1976 | United Kingdom | . |

OTHER PUBLICATIONS

Wertheim, "Organic Chemistry", pp. 632–533 (1951).
Patai, "The Chemistry of the Amino Group", pp. 669–671, 685–687 (1968).
Helb, Chim. Acta 19, 1034 (1936).
Patai reference and Karrer, et al, "Helcetica Chemica Acta", vol. XIX, pp. 1034–1043 (1936).
Astle, "Industrial Organic Nitrogen Compounds", pp. 314–315 (1961).
Chem. Ber. 83, 409 (1950) from Chemical Abstracts, vol. 44, 10 051d (1950).

*Primary Examiner*—Charles F. Warren
*Assistant Examiner*—John A. Sopp
*Attorney, Agent, or Firm*—Sprung Horn Kramer & Woods

[57] ABSTRACT

Process for the preparation of a nitroaminobenzene by nitrating an aminobenzene which is protected at the nitrogen wherein the nitration is carried out by the simultaneous combination of nitric acid and the aminobenzene to be nitrated, in the presence of inert solvents such as methylene chloride.

47 Claims, No Drawings

PROCESS FOR THE PREPARATION OF NITROAMINOBENZENES

CROSS-REFERENCE TO RELATED APPLICATIONS

This patent application is a continuation-in-part of copending patent applications Ser. No. 359,331, filed Mar. 18, 1982, now abandoned (which is a continuation of patent application Ser. No. 199,888, filed Oct. 23, 1980, now abandoned); Ser. No. 199,889 filed Oct. 23, 1980, now abandoned; and Ser. No. 199,876 filed Oct. 23, 1980, now abandoned.

BACKGROUND OF THE INVENTION

The present invention relates to a process for the preparation of nitroaminobenzenes from aminobenzenes which are protected at the nitrogen, by nitration in the presence of inert, water-immiscible organic solvent and/or diluents.

It is known to prepare nitroacylaminobenzenes and the corresponding nitroaminobenzenes by employing a one-vessel process, starting from aminobenzenes, first reacting these with acylating agents, such as acetic anhydride, benzoyl chloride or p-toluenesulphonic acid chloride, in the presence of inert organic solvents, preferably in monochlorobenzene, at an elevated temperature, and then nitrating the products, without intermediate isolation, at 25° to 50° C. (compare U.S. Pat. No. 2,459,002, Examples 1 to 8).

Disadvantages of the process described in the U.S. patent specification are the low yields and poor qualities of nitroaminobenzenes, as is shown by repeating Examples 2 and 4 of the U.S. patent specification (since the examples of the U.S. patent specification themselves do not state the yield and product quality).

Since, in the process of U.S. Pat. No. 2,459,002, the acylation and nitration are carried out successively, that is to say without isolation of the acylated intermediate product, the nitration mixture always consists of excess acylating agent, liberated organic or inorganic acid, and nitric acid. This however has the disadvantage, in addition to the low yields and poor qualities of nitroaminobenzenes, that on subsequent neutralization of the reaction mixture more alkali is required than is actually needed for the neutralization of the nitric acid. As a result of the neutralization, the excess acylating agent and the organic or inorganic acid liberated are lost to subsequent economical utilization and furthermore the effluent is polluted by the salts formed during the neutralization.

A further disadvantage of the process described in the U.S. patent specification is that if the subsequent removal of the protective group is carried-out, without intermediate isolation of the nitroacylamino compounds, in an acid medium in the nitration mixture which has beforehand been neutralized and freed from chlorobenzene, large amounts of sulphuric acid are required (compare, in this context, U.S. Pat. No. 2,459,002, Examples 4 and 7, where, respectively, 6.6 and 4.4 mols of sulphuric acid are employed per mol of aminobenzene). Since, in this process, the removal of the protective group must furthermore be carried out in concentrated sulphuric acid, it is necessary that the sulphuric acid should, for isolation of the nitroaminobenzenes, first be diluted with water and then be neutralized with sodium carbonate. This produces large amounts of salt-containing effluents, which must be disposed of, or worked up, at considerable expense.

It has furthermore been observed, on repeating Examples 2 and 4 of U.S. Pat. No. 2,459,002 that, if 5-nitro-2-acetylaminoanisole or 3-nitro-4-acetylaminotoluene are cleaved in an acid medium, without intermediate isolation, some resinification occurs. To isolate the 5-nitro-2-aminoanisole or the 3-nitro-4-aminotoluene it is therefore necessary first to treat the reaction solution with active charcoal.

Further, it is known to prepare 3-nitro-4-aminoanisole by starting from 4-acetylaminoanisole, metering this, simultaneously with about 61.5% strength aqueous nitric acid, in the course of about 3 hours into an initial charge of monochlorobenzene, which already contains a part of the nitric acid required for the nitration, together with major amounts of sodium chloride, at 20° to 30° C. and cleaving the completely reacted nitration mixture with alkali, without intermediate isolation of the 3-nitro-4-acetylaminoanisole, after having neutralized the excess nitric acid and distilled the monochlorobenzene in steam (compare Bios Final Report No. 986, page 285–288).

An important disadvantage of this process is to be found in the fact that the nitration is carried out in the presence of large amounts of sodium chloride, whereby the effluent formed is additionally polluted. A further pollution of the effluent results from the sodium nitrate formed on neutralization of the excess nitric acid.

It is a further disadvantage that the chlorobenzene is removed from the nitration mixture, which has first been rendered slightly alkaline with sodium carbonate, by an energy-consuming steam distillation lasting about 5 hours, before the protective group is split off with alkali. Furthermore, the yields and qualities of 3-nitro-4-aminoanisole achieved are unsatisfactory.

It is known to prepare 3-nitro-4-aminotoluene by nitrating 4-acetylaminotoluene with the aid of an acid mixture containing nitric acid and sulphuric acid, in an inert solvent, such as methylene chloride (German Auslegeschrift (German Published Specification) No. 2,226,405).

However, this process has the disadvantage that in addition to the desired 3-nitro-4-acetylaminotoluene, 2-nitro-4-acetylaminotoluene is also formed as a by-product, and this, after alkaline desacetylation, detracts from the quality of the 3-nitro-4-aminotoluene.

Furthermore, the yields of the desired reaction product, namely 88–91% of theory, are unsatisfactory for a commercial process.

SUMMARY OF THE INVENTION

The present invention concerns a process for the preparation of nitroaminobenzenes by nitrating aminobenzenes (starting material), which are protected at the nitrogen of the starting material, by simultaneously introducing into a reaction vessel containing one or more inert solvents and/or diluents, a nitric acid and the aminobenzene to be nitrated.

The present invention also concerns a process for the preparation of nitroaminobenzenes by nitrating aminobenzenes, which are protected at the nitrogen, by simultaneously combining 50% to 100% strength by weight nitric acid and the aminobenzene to be nitrated in the presence of inert, water-immiscible organic solvents and/or diluents, optionally in the presence of nitrous acid and/or of substances which form nitrous acid, and optionally in the presence of water-binding agents, at temperatures of 0° C. to 80° C. After the nitroaminobenzene is prepared, the protective group of the nitroaminobenzenes is then split off, optionally after prior removal of the organic solvents and/or diluents, and the nitroaminobenzenes are then isolated.

In a preferred embodiment of the above process according to the invention, the excess nitric acid is removed, after completion of nitration, completely or partially from the nitration mixture, optionally after prior neutralization of the nitric acid, thereafter the protective group of the nitroaminobenzenes is split off optionally after prior removal of the methylene chloride, and the nitroaminobenzenes are isolated.

In a particularly preferred procedure of the above process according to the invention, the excess nitric acid is removed, after completion of nitration, completely or partially from the nitration mixture, optionally after the prior neutralization of the nitric acid and optionally after a phase separation, by means of extraction with water.

The present invention further relates to a process for the preparation of 3-nitro-4-amino toluene by nitration of 4-tolylcarbamic acid esters and subsequent alkaline saponification and working up of the reaction products, which process is characterized in that the nitration is carried out by simultaneously combining nitric acid and 4-tolylcarbamic acid esters in the presence of an inert, water-immiscible organic solvent and/or diluent or mixture thereof, with 50 to 100% strength by weight nitric acid, at temperatures in the range from −10° C. to +45° C.

This invention also is directed to a process for the preparation of 3-nitro-4-aminotoluene by nitration of p-acetylaminotoluene in the presence of inert, water-immiscible organic solvents at a temperature in the range from 0° C. to 80° C. and by subsequent alkaline saponification and working up of the reaction product, which process is characterized in that the nitration is carried out by simultaneously combining p-acetylaminotoluene and 60% to 100% strength by weight nitric acid in the presence of methylene chloride.

DETAILED DESCRIPTION OF THE INVENTION

According to the present invention as aminobenzenes protected at the nitrogen, it is possible to employ those of the general formula (I)

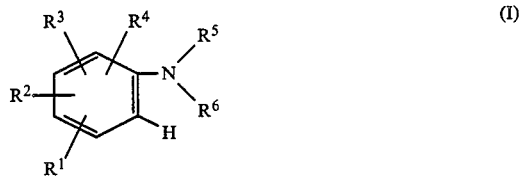

wherein
R$^1$ to R$^4$ are identical or different and represent 1 to 4 hydrogen atoms, 1 to 4 halogen atoms, 1 to 4 alkyl radicals, 1 to 2 alkoxy radicals, 1 to 2 acyloxy radicals, 1 to 2 aryloxy radicals, an acylamino radical, a carboxyl radical, an alkoxycarbonyl radical, an alkylsulphonyl radical, an aralkoxy radical, an aralkylsulphonyl radical, an arylsulphonyl radical, a hydroxysulphonyl radical or an aminosulphonyl radical, R$^5$ denotes hydrogen and
R$^6$ denotes formyl, oxalyl, alkylcarbonyl, alkylsulphonyl, organoxycarbonyl such as those of the formula

—C—OR wherein R represents cycloaliphatic or aliphatic radical of 1 to 8 carbon atoms, e.g., alkoxycarbonyl, or R$^6$ denotes arylcarbonyl, arylsulphonyl or

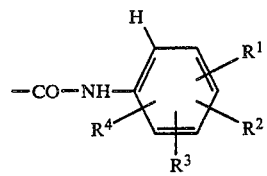

wherein
R$^1$ to R$^4$ are identical or different and have the above-mentioned meaning,
R$^6$ denotes

—CO—NH—R' wherein
R' is hydrogen or alkyl, preferably hydrogen, and preferably
R$^6$ represents alkylcarbonyl, alkylsulphonyl, alkoxycarbonyl, arylcarbonyl or arylsulphonyl, particularly preferentially alkylcarbonyl or alkoxycarbonyl,
R$^5$ and R$^6$ together represent a phthalyl radical
R$^5$ and R$^6$ conjointly with a ring carbon atom which is in the ortho-position to the carbon atom substituted by the protected amino group form a 2-methyl-substituted oxazole ring, an oxazolone ring or a 2,6-dioxo-dihydro-1,3-oxazine ring, in which case, at the same time, one of the radicals R$^1$ to R$^4$ other than hydrogen must be present in the para-position to the ring carbon atom which is substituted by the protected amino group.

Aminobenzenes preferably employed in the process according to the invention are those of the general formula (II)

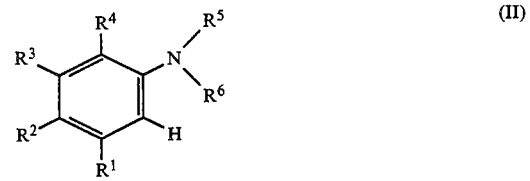

wherein
R$^1$ represents hydrogen, halogen, alkyl or alkoxy, preferably halogen, alkyl or alkoxy;
R$^2$ represents hydrogen, halogen, alkyl, alkoxy, acyloxy, acylamino, alkylsulphonyl, arylsulphonyl, aryloxy, carboxyl or hydroxysulphonyl, preferably halogen, alkyl, alkoxy, acyloxy, acylamino, alkylsulphonyl or arylsulphonyl;

$R^3$ represents hydrogen, halogen, alkyl, alkoxy, acyloxy or acylamino, preferably halogen, alkyl, alkoxy, acyloxy or acylamino;

$R^4$ represents hydrogen, halogen, alkyl, alkoxy, aryloxy or carboxyl, preferably hydrogen, halogen, alkyl or alkoxy;

$R^5$ denotes hydrogen and $R^6$ represents formyl, oxalyl, alkylcarbonyl, alkylsulphonyl, alkoxycarbonyl, arylcarbonyl, arylsulphonyl or

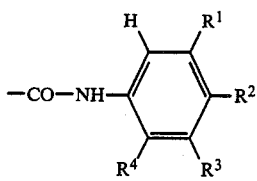

wherein $R^1$ to $R^4$ are identical or different and have the previously mentioned meaning, or $R^6$ represents

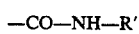

—CO—NH—R' wherein

R' is hydrogen or alkyl, preferably hydrogen, and preferably $R^6$ represents alkylcarbonyl, alkylsulphonyl, alkoxycarbonyl, arylcarbonyl or arylsulphonyl, particularly preferentially alkylcarbonyl or alkoxycarbonyl, or $R^5$ and $R^6$ together represent a phthalyl radical or $R^5$ and $R^6$ conjointly with a ring carbon atom which is in the ortho-position to the carbon atom substituted by the protected amino group form a 2-methyl-substituted oxazole ring, an oxazolone ring or a 2,6-dioxo-dihydro-1,3-oxazine ring, in which case, at the same time, one of the radicals $R^1$ to $R^4$ other than hydrogen must be present in the para-position to the ring carbon atom which is substituted by the protected amino group.

As aminobenzenes protected at the nitrogen it is furthermore possible to employ those of the general formula (III)

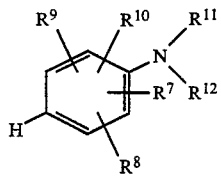

wherein $R^7$ to $R^{10}$ are identical or different and represent 1 to 4 hydrogen atoms, 1 to 4 halogen atoms, 1 to 4 alkyl radicals, 1 to 2 alkoxy radicals, 1 to 2 acyloxy radicals, 1 to 2 aryloxy radicals, an acylamino radical, a carboxyl radical, an alkoxycarbonyl radical, an alkylsulphonyl radical, an aralkoxy radical, an aralkylsulphonyl radical, an arylsulphonyl radical, a hydroxysulphonyl radical or an aminosulphonyl radical, $R^{11}$ denotes hydrogen and $R^{12}$ denotes formyl, oxalyl, alkylcarbonyl, alkylsulphonyl, alkoxycarbonyl, arylcarbonyl, arylsulphonyl or

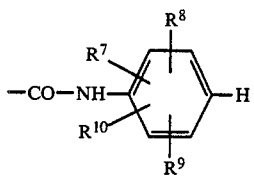

wherein $R^7$ to $R^{10}$ are identical or different and have the previously mentioned meaning, or $R^{12}$ denotes

—CO—NH—R' wherein

R' represents hydrogen or alkyl, preferably hydrogen, and preferably $R^{12}$ represents alkylcarbonyl, alkylsulphonyl, alkoxycarbonyl, arylcarbonyl or arylsulphonyl, particularly preferentially alkylcarbonyl or alkoxycarbonyl, or $R^{11}$ and $R^{12}$ together represent a phthalyl radical or $R^{11}$ and $R^{12}$, conjointly with a ring carbon atom which is in the ortho-position to the carbon atom substituted by the protected amino group form a 2-methyl-substituted oxazole ring, an oxazolone ring or a 2,6-dioxo-dihydro-1,3-oxazine ring.

As preferred aminobenzenes, there are employed those of the general formula (IV)

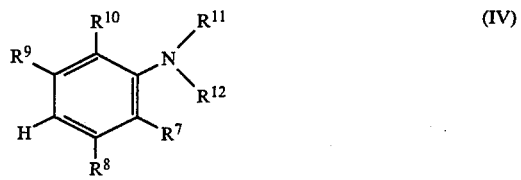

wherein $R^7$ represents hydrogen, halogen, alkyl, alkoxy, acyloxy, acylamino, carboxyl, alkyl, arylsulphonyl or aryloxy, preferably halogen, alkyl, alkoxy, acyloxy, acylamino, alkylsulphonyl or arylsulphonyl, $R^8$ represents hydrogen, halogen, alkyl, alkoxy, alkoxycarbonyl, acyloxy, acylamino, carboxyl, alkylsulphonyl or arylsulphonyl, preferably hydrogen, halogen, alkyl, alkoxy, acyloxy or acylamino, $R^9$ represents hydrogen, halogen, alkyl, alkoxy, alkoxycarbonyl, acyloxy, acylamino, alkylsulphonyl, arylsulphonyl or aralkylsulphonyl, preferably hydrogen, halogen, alkyl, alkoxy, alkoxycarbonyl, acyloxy or acylamino, $R^{10}$ represents hydrogen, halogen or alkyl, $R^{11}$ denotes hydrogen and $R^{12}$ denotes formyl, oxalyl, alkylcarbonyl, alkyl-, sulphonyl, alkoxycarbonyl, arylcarbonyl, acylsulphonyl or

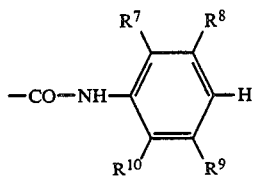

wherein
R$^7$ to R$^{10}$ are identical or different and have the previously mentioned meaning, or
R$^{12}$ represents

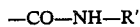

wherein
R' represents hydrogen or alkyl, preferably hydrogen, and preferably
R$^{12}$ represents alkylcarbonyl, alkylsulphonyl, alkoxycarbonyl, arylcarbonyl or arylsulphonyl, particularly preferentially alkylcarbonyl or alkoxycarbonyl, or
R$^{11}$ and R$^{12}$ together represent a phthalyl radical or
R$^{11}$ and R$^{12}$ conjointly with a ring carbon atom which is in the ortho-position to the carbon atom substituted by the protected amino group form a 2-methyl-substituted oxazole ring, an oxazolone ring or a 2,6-dioxo-dihydro-1,3-oxazine ring.

Suitable halogens of the formula (I) to (IV) are fluorine, chlorine or bromine, preferably fluorine or chlorine, especially chlorine; suitable alkyl radicals are those with 1 to 12, preferably 1 to 6, carbon atoms, which can optionally be substituted by halogen, such as fluorine, chlorine or bromine, and/or by alkoxy groups, such as methoxy, ethoxy, propoxy or butoxy, examples being the methyl, trifluoromethyl, ethyl, n-propyl, iso-propyl, n-butyl, iso-butyl, tert.-butyl, n-pentyl, iso-pentyl, n-hexyl and the cyclohexyl radical, preferably the methyl, trifluoromethyl, ethyl, n-propyl, iso-propyl, n-butyl, iso-butyl and the tert.-butyl radical, especially the methyl, trifluoromethyl and the ethyl radical.

As alkoxy radicals of the formula (I) to (IV), which can optionally be substituted by a carboxyl group, there may be mentioned those with 1 to 6, preferably 1 to 4, carbon atoms, or those of the formula

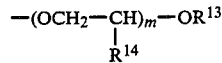

wherein
R$^{13}$ denotes an alkyl radical with 1 to 6, preferably 1 to 4, carbon atoms, or an acyl radical with 1 to 7, preferably 1 to 4, carbon atoms, and
R$^{14}$ represents hydrogen or methyl, preferably hydrogen and m can be an integer from 1 to 6, preferably 1 to 2.

The following alkoxy radicals may be mentioned as examples:
—OCH$_3$, —OC$_2$H$_5$, —OC$_3$H$_7$, —OC$_4$H$_9$, —OCH$_2$CH$_2$OCH$_3$, —OCH$_2$CH$_2$OC$_2$H$_5$, —OCH$_2$CH$_2$OC$_3$H$_7$, —OCH$_2$CH$_2$OC$_4$H$_9$, —(OCH$_2$CH$_2$)$_2$OCH$_3$, —(OCH$_2$—CH$_2$)$_2$OC$_2$H$_5$, —(OCH$_2$CH$_2$)$_2$OC$_3$H$_7$, —(OCH$_2$CH$_2$)$_2$OC$_4$H$_9$, —OCH$_2$CH$_2$OCOCH$_3$, —OCH$_2$CH$_2$OCOC$_2$H$_5$, —OCH$_2$CH$_2$OCOC$_3$H$_7$, —OCH$_2$CH$_2$OCOC$_4$H$_9$, —(OCH$_2$CH$_2$)$_2$OCOCH$_3$, —(OCH$_2$CH$_2$)$_2$OCOC$_2$H$_5$, —(OCH$_2$CH$_2$)$_2$OCOC$_3$H$_7$, —(OCH$_2$CH$_2$)$_2$OCOC$_4$H$_9$,

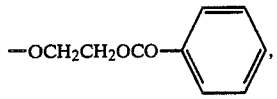

preferably —OCH$_3$, OC$_2$H$_5$, —OCH$_2$CH$_2$OCH$_3$, —OCH$_2$CH$_2$OC$_2$H$_5$, —O(CH$_2$CH$_2$)$_2$OCH$_3$, —(OCH$_2$CH$_2$)$_2$OC$_2$H$_5$, —OCH$_2$CH$_2$OCOCH$_3$, —(OCH$_2$CH$_2$)$_2$OCOCH$_3$.

As acyloxy radicals of the formula (I) to (IV) there may be mentioned those in which the acyl radical denotes an alkylcarbonyl radical with 2 to 7, preferably 2 to 5, carbon atoms, or a benzoyl radical, which can optionally be substituted by halogen, such as fluorine, chlorine or bromine, by a nitro group, by a methyl radical or by a methoxy radical. The following acyloxy radicals may be mentioned as examples: —OCOCH$_3$, —OCOC$_2$H$_5$, —OCOC$_3$H$_7$, —OCOC$_4$H$_9$,

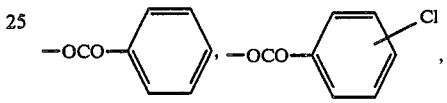

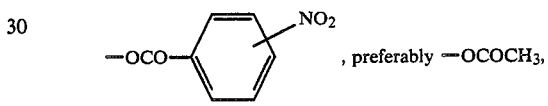

, preferably —OCOCH$_3$,

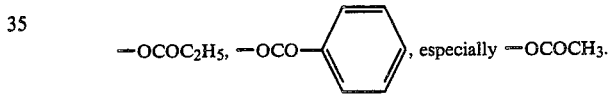

, especially —OCOCH$_3$.

As acylamino radicals of the formula (I) to (IV) there may be mentioned those in which the acyl radical denotes a formyl radical, an alkylcarbonyl radical with 2 to 7, preferably 2 to 5, carbon atoms, or a benzoylyl radical which can optionally be substituted by halogen, such as fluorine, chlorine or bromine, by a nitro group, by a methyl radical or by a methoxy radical.

The following acylamino radicals may be mentioned:
—NHCOH, —NHCOCH$_3$, —NHCOC$_2$H$_5$, —NHCOC$_3$H$_7$, —NHCOC$_4$H$_9$,

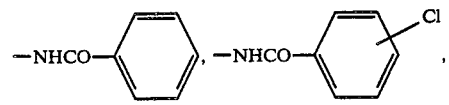

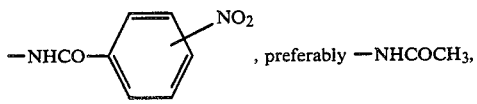

, preferably —NHCOCH$_3$,

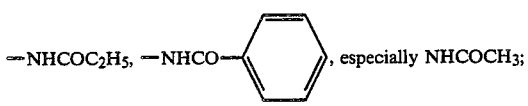

, especially NHCOCH$_3$;

suitable alkoxycarbonyl radicals of the formula (I) to (IV) are those with 2 to 7, preferably 2 to 5, carbon atoms, for example methoxycarbonyl, ethoxycarbonyl, propoxycarbonyl and butoxycarbonyl, preferably methoxycarbonyl and ethoxycarbonyl;

suitable alkylsulphonyl radicals of the formula (I) to (IV) are those with 1 to 6, preferably 1 to 4, carbon atoms, such as methylsulphonyl, ethylsulphonyl, propylsulphonyl and butylsulphonyl, preferably methylsulphonyl.

Possible aralkoxy radicals of aralkylsulphonyl radicals of the formula (I) to (IV), which can optionally be monosubstituted or polysubstituted by halogen, such as fluorine, chlorine or bromine, and/or by a nitro group and/or by an alkyl and/or by an alkoxy group with 1 to 6, preferably 1 to 4, carbon atoms, are those with 7 to 17, preferably 7 to 13, carbon atoms. As examples there may be mentioned:

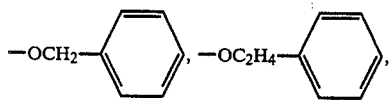

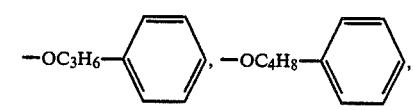

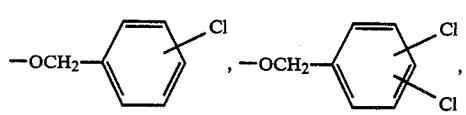

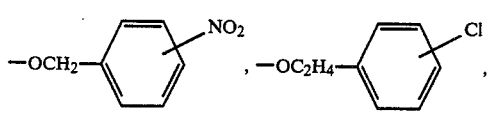

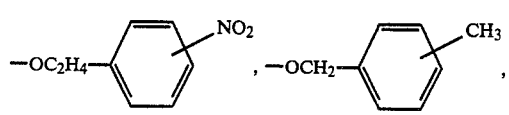

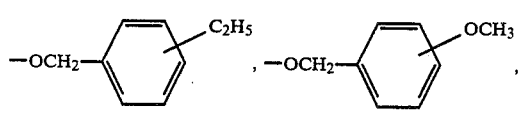

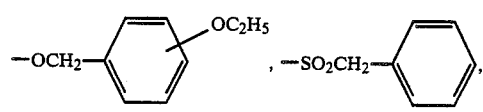

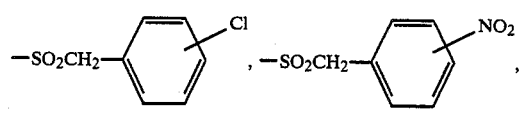

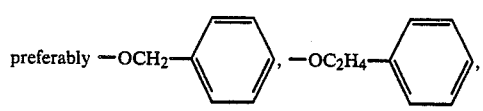

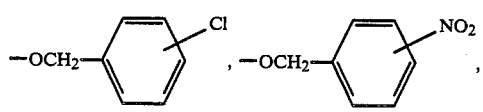

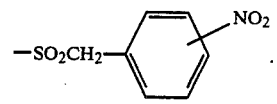

Possible aryloxy or arylsulphonyl radicals of the formula (I) to (IV), which can optionally be monosubstituted or polysubstituted by halogen, such as fluorine, chlorine or bromine, and/or by a nitro group and/or by an alkyl radical and/or alkoxy radical with 1 to 6, preferably 1 to 4, carbon atoms, are those with 6 to 12, preferably 6 to 10, carbon atoms. As examples there may be mentioned:

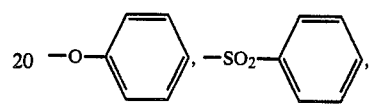

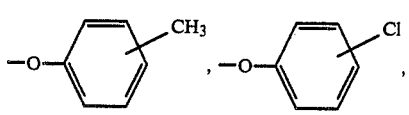

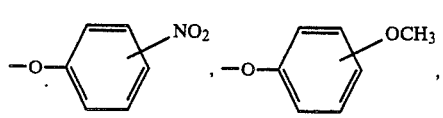

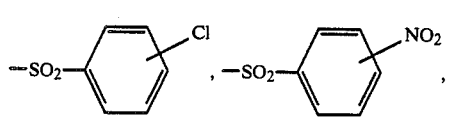

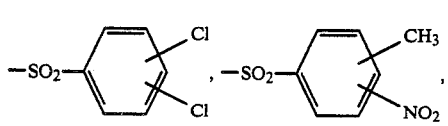

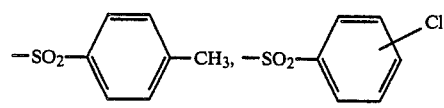

As alkylcarbonyl radicals, which can optionally be monosubstituted or polysubstituted by halogen, such as fluorine, chlorine or bromine, there may be mentioned those with 2 to 7, preferably 2 to 5, carbon atoms, such as acetyl, ethylcarbonyl, propylcarbonyl, butylcarbonyl and trifluoroacetyl, preferably acetyl and ethylcarbonyl, and especially acetyl.

As arylcarbonyl radicals, which can optionally be monosubstituted or polysubstituted by halogen, such as fluorine, chlorine or bromine, and/or by a nitro group and/or by an alkyl radical and/or alkoxy radical with 1 to 6, preferably 1 to 4, carbon atoms, there may be mentioned those with 7 to 13, preferably 7 to 11, carbon atoms, such as

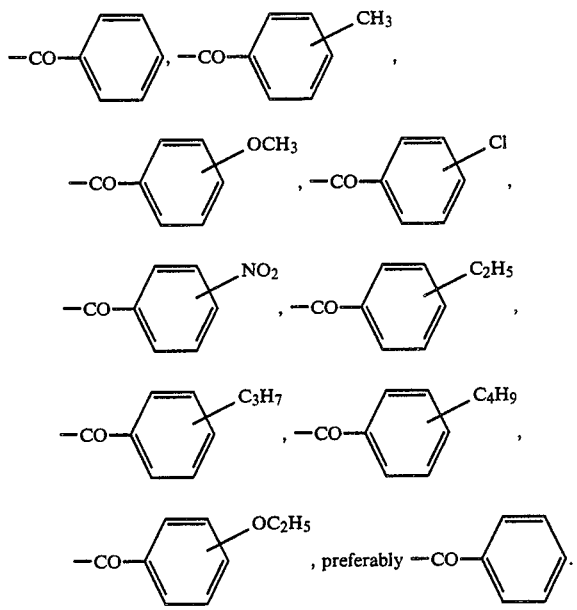

Possible aminosulphonyl radicals of the formula (I) to (IV), which can optionally be substituted by alkyl radicals with 1 to 6, preferably 1 to 4, carbon atoms, are the methylaminosulphonyl, the ethylaminosulphonyl, the propylaminosulphonyl and the butylaminosulphonyl radical, preferably the methylaminosulphonyl radical and the ethylaminosulphonyl radical.

Compounds preferably employed in the process according to the invention are those of the formulae

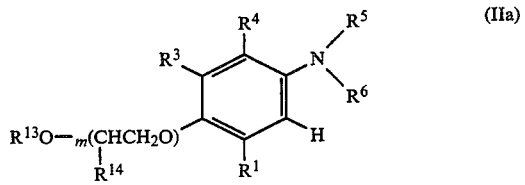

and

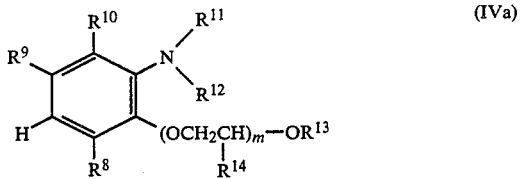

wherein $R^1$, $R^3$, $R^4$, $R^8$, $R^9$ and $R^{10}$ are identical or different and represent 1 to 3 hydrogen atoms, 1 to 2 halogen atoms, 1 to 2 alkyl radicals or 1 to 2 alkoxy radicals, and the radicals $R^5$, $R^6$, $R^{11}$, $R^{12}$, $R^{13}$ and $R^{14}$, as well as m, have the meaning of the corresponding radicals of the previously mentioned formula (I–IV).

Preferably, the following aminobenzenes, protected at the nitrogen, are employed in the process according to the invention: N-(4-bromophenyl)-acetamide, N-(4-chloro-6-trifluoromethylphenyl)-acetamide, N-(4-chloro-5-trifluoromethylphenyl)-acetamide, N-(5-chloro-4-fluorophenyl)-acetamide, N-(4-chloro-3,5-dimethylphenyl)-acetamide, N-(4-bromo-3,5-dimethyl)-acetamide, N-(4,6-dichloro-3,5-dimethylphenyl)-acetamide, N-(4-chloro-3,6-dimethylphenyl)-acetamide, N-(4-methylphenyl)-benzenesulphonamide, N-(4-methylphenyl)-p-toluenesulphonamide, N-(4-methoxyphenyl)-acetamide, N-(4-methoxyphenyl)-benzenesulphonamide, N-(4-methoxyphenyl)-p-toluenesulphonamide, 4-methoxyphenyl-carbamic acid methyl ester, 4-methoxyphenyl-carbamic acid ethyl ester, N-(4-ethoxyphenyl)-acetamide, N-(4-ethoxyphenyl)-benzenesulphonamide, N-(4-ethoxyphenyl)-p-toluenesulphonamide, 4-ethoxyphenyl-carbamic acid methyl ester, 4-ethoxyphenylcarbamic acid ethyl ester, N-(4-ethoxy-6-methylphenyl)-acetamide, N-(4-methoxy-6-methylphenyl)-acetamide, N-(4,6-dimethoxyphenyl)-acetamide, N-(4-acetoxy-6-methylphenyl)-acetamide, N-[[4-[2-(2-methoxyethoxy)]-ethoxyphenyl]]-acetamide, N-(acetoxyphenyl)-acetamide, 6-chloro-benzoxazolone, 6-chloro-2-methyl-benzoxazole, 6-methyl-benzoxazolone, 6,2-dimethyl-benzaoxazole, N-(4,6-dimethylphenyl)-acetamide, 4-acetylaminobenzoic acid, N-(5-acetylamino-4-methylphenyl)-acetamide, N-(4-acetylaminophenyl)-acetamide, N-(4-acetylamino-6-methylphenyl)-acetamide, N-(6-bromo-4-methylphenyl)-acetamide, N-(4-chlorophenyl)-acetamide, N-(4,6-dichlorophenyl)-acetamide, N-(4,5-dichlorophenyl)-acetamide, N-(4-bromo-5-methylphenyl)-acetamide, N-(4,6-dichloro-5-methylphenyl)-acetamide, N-(5-fluoro-4-methylphenyl)-acetamide, N-(5-chloro-4-methylphenyl)-acetamide, N-(4,5-dimethylphenyl)-acetamide, N-(4-chloro-5,6-dimethylphenyl)-acetamide, N-(5-bromo-4,6-dimethylphenyl)-acetamide, N-(4-ethylphenyl)-acetamide, N-(4-tert.-butylphenyl)-acetamide, N-(4-ethyl-6-methylphenyl)-acetamide, N-(5-chlorophenyl)-acetamide, N-(5-methylphenyl)-acetamide, N-(5-methoxyphenyl)-acetamide, N-(5-fluorophenyl)-acetamide, N-(3,4,6-trichlorophenyl)-acetamide, N-(4-chloro-6-methylphenyl)-acetamide, N-(3,4-dichloro-6-methoxyphenyl)-acetamide, N-(5-chloro-4-methoxyphenyl)-acetamide, N-(4-chloro-3,6-diethoxyphenyl)-acetamide, 6-chloroisatoic anhydride, 6-methylisatoic anhydride, N-(4-methylsulphonylphenyl)-acetamide, N-(2-methylphenyl)-acetamide, N-(2-methylphenyl)-benzenesulphonamide, N-(2-methylphenyl)-p-toluenesulphonamide, 2-methylphenyl-carbamic acid methyl ester, 2-methylphenyl-carbamic acid ethyl ester, N-(2-acetoxyphenyl)-acetamide, 2-methylbenzoxazole, benzoxazolone, N-(2-methoxyphenyl)-acetamide, N-(2-methoxyphenyl)-benzenesulphonamide, 2-methoxyphenylcarbamic acid methyl ester, 2-methoxyphenyl-carbamic acid ethyl ester, N-(2-methoxyphenyl)-oxamic acid, N-(2-ethoxyphenyl)-acetamide, 2-ethoxyphenyl-carbamic acid methyl ester, 2-ethoxyphenyl-carbamic acid ethyl ester, N-(2-ethoxyphenyl)-benzenesulphonamide, N-[[2-[2-(2-methoxyethoxy)]-ethoxyphenyl]]-acetamide, N-(5-chloro-2-methylphenyl)-acetamide, N-(5-chloro-2-methylphenyl)-benzenesulphonamide, N-(2-benzenesulphonylphenyl)-acetamide, N-(2-benzenesulphonylphenyl)-methylsulphonamide, 2-acetylaminobenzoic acid, N-(5-chloro-2-methoxyphenyl)-benzamide, N-(5-chloro-2-methoxyphenyl)-acetamide, N-(2-chloro-5-methylphenyl)-acetamide, N-(2-chloro-5-methylphenyl)-benzamide, N-(2,5-dichlorophenyl)-acetamide, N-(2,3-dichlorophenyl)-acetamide, N-(2-chlorophenyl)-acetamide, N-(2,6-dichlorophenyl)-acetamide, N-(2-bromophenyl)-acetamide, N-(2-fluorophenyl)-acetamide, N-(2-acetylaminophenyl)-acetamide, N-(5-acetylamino-2-methylphenyl)-acetamide, N-(2-acetoxy-5-chlorophenyl)-acetamide, N-(2-methanesulphonylphenyl)-acetamide, N-(2-methoxy-5-methylphenyl)-acetamide, N-(2,5-dimethoxyphenyl)-acetamide, N-(2,5-diethoxyphenyl)-acetamide, (2-acetylaminophenoxy)-acetic acid, N-(2,3-dimethylphenyl)-acetamide, N-(2,6-dimethylphenyl)-acetamide, N-(2,5-dimethylphenyl)-acetamide, N-(3,5-dimethylphenyl)-acetamide, N-(2-chloro-6-methylphenyl)-acetamide, N-(2-chloro-5-trifluoromethyl)-acetamide, N-(2-benzenesulphonyl-5-trifluoromethyl)-acetamide, N-(5-ethanesulphonyl-2-methoxyphenyl)-acetamide and isatoic anhydride.

Particularly preferentially, the following compounds are employed in the process according to the invention: N-(4-methoxyphenyl)-acetamide, 4-methoxyphenyl-carbamic acid methyl ester and ethyl ester, N-(4-ethoxyphenyl)-acetamide, 4-ethoxyphenyl-carbamic acid methyl ester and ethyl ester, N-[[4-[2-(2-methoxyethoxy)]-ethoxyphenyl]]-acetamide, N-(4-acetoxyphenyl)-acetamide, N-(4,6-dimethylphenyl)-acetamide, N-(4-acetylaminophenyl)-acetamide, N-(4-chlorophenyl)-acetamide, N-(4,6-dichlorophenyl)-acetamide, N-(5-chlorophenyl)-acetamide, N-(5-fluorophenyl)-acetamide, N-(2-methylphenyl)-benzenesulphonamide, 2-methylphenylcarbamic acid methyl ester and ethyl ester, N-(2-acetoxyphenyl)-acetamide, 2-methylbenzoxazole, benzoxazolone, N-(2-methoxyphenyl)-acetamide, N-(2-methoxyphenyl)-benzenesulphonamide, 2-methoxyphenyl-carbamic acid methyl ester and ethyl ester, N-[[2-[2-(2-methoxy-ethoxy)]ethoxy)]-ethoxyphenyl]]-acetamide, N-(5-chloro-2-methylphenyl)-acetamide, N-(5-chloro-2-methylphenyl)-benzenesulphonamide, N-(5-chloro-2-methoxyphenyl)-acetamide, N-(5-chloro-2-methoxyphenyl)-benzamide, N-(2-chloro-5-methylphenyl)-benzamide, N-(2,5-dichlorophenyl)-acetamide, N-(2,3-dichlorophenyl)-acetamide, N-(2-chlorophenyl)-acetamide, N-(2-bromophenyl)-acetamide, N-(2,6-dichlorophenyl)-acetamide, N-(2-acetylaminophenyl)-acetamide, N-(2-acetoxy-5-chlorophenyl)-acetamide, N-(2-methanesulphonylphenyl)-acetamide, N-(2-methoxy-5-methylphenyl)-acetamide, N-(2,5-dimethoxyphenyl)-acetamide and N-(2,5-diethoxyphenyl)-acetamide.

4-tolylcarbamic acid esters of the general formula

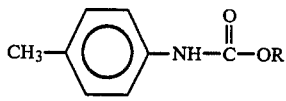

may be employed as aminobenzines according to the present invention
wherein
R represents a cycloaliphatic or aliphatic radical with 1 to 8 carbon atoms, preferably 1 to 6 carbon atoms, especially cycloalkyl and alkyl radicals may be employed in the process according to the invention.

As cycloaliphatic radicals there may be mentioned: cyclopentyl, cyclohexyl, cycloheptyl, 1-, 2- and 3-methylcyclopentyl and 1- and 2-methylcyclohexyl, cyclohexyl being preferred; as aliphatic radicals there may be mentioned: methyl, ethyl, n-propyl, iso-propyl, n-butyl, iso-butyl, tert.-butyl, n-pentyl, iso-pentyl, n-hexyl, iso-hexyl and 2,2-dimethyl-but-3-yl, methyl and ethyl being preferred.

4-Tolylcarbamic acid esters preferentially employed in the process according to the invention are those whose aliphatic or cycloaliphatic radicals can, after the cleavage reaction, easily be removed from the reaction mixture either by distillation, phase separation and/or extraction.

By way of example, the following tolylcarbamic acid esters may be employed: 4-tolylcarbamic acid methyl, ethyl, n-propyl, iso-propyl, tert.-butyl, n-butyl, iso-butyl, n-pentyl, iso-pentyl, n-hexyl and cyclohexyl ester. The methyl and ethyl ester of 4-tolylcarbamic acid are particularly preferentially employed.

When employing p-acetylaminotoluene as a starting material, either technical grade p-acetylaminotoluene with a content of about 96 to 99.5% by weight or pure p-acetylaminotoluene with a content of $\geqq 99.5\%$ by weight can be employed as the feed materials in the process according to the invention. Before it is reacted, technical grade p-acetylaminotoluene can, for example, be washed with methylene chloride or recrystallized for purification.

The nitric acid is preferably employed in a concentration of 50 to 100% by weight, preferably 65 to 100% by weight, particularly preferentially in a concentration of 80 to 98% by weight, in the process according to the invention. Nitric acid in a concentration of 65 to 100% by weight is preferred when the starting material is a tolylcarbamic acid ester and 85 to 100% by weight nitric acid is preferred when the starting material is p-acetylaminotoluene. Nitration with 98% strength nitric acid being particularly preferred in some instances such as when the starting material is a 4-tolylcarbamic acid ester or p-acetylaminotoluene. The process can be carried out in the absence of sulfuric acid.

The amount of nitric acid required for nitration in the process according to the invention depends, for example, on the concentration of the acid, the nitration temperature and the nature of the protective group bonded to the nitrogen.

In general, at least 1.1 mols of 100% strength by weight nitric acid, preferably 1.1 to 9 mols, particularly preferentially 1.2 to 7 mols, of 100% strength by weight nitric acid are employed, in the process according to the invention, per mol of starting material.

According to the process of the invention when 4-tolylcarbamic acid ester is the starting material, at least 1.5 mols of 100% strength by weight nitric acid, preferably 1.5 to 5 mols and especially preferentially 1.6 to 3.5 mols of 100% strength by weight nitric acid, are employed per mol of 4-tolylcarbamic acid ester.

When p-acetylaminotoluene is the starting material at least 2 mols of 100% strength by weight nitric acid, preferably 2 to 6 mols and particularly preferably 2.2 to 4.5 mols of 100% strength by weight nitric acid, per mol of p-acetylaminotoluene are employed in the process according to the invention.

If dehydrating agents, such as phosphorus pentoxide, are used, it is also possible, if desired, to work with molar amounts of nitric acid.

If 50% strength by weight nitric acid is employed, in general at least 1.3 mols of nitric acid are used per mol of starting material. Preferably, 1.3 to 15 mols, particularly preferentially 1.4 to 12 mols, of 50% strength nitric acid are employed per mol of starting material. For nitric acid concentrations which lie between 50 and 100% by weight it is expedient to determine the most advantageous molar ratio of nitric acid to starting compound by preliminary experiments.

When using 50% strength by weight nitric acid at least 3 mols of nitric acid are employed per mol of 4-tolylcarbamic acid ester. Preferably, 3 to 10 mols, particularly preferentially 3.5 to 7 mols, of 50% strength by weight nitric acid are employed per mol of 4-tolylcarbamic acid ester. For nitric acid concentrations which are between 50 and 100% by weight, the most favorable molar ratio of nitric acid to 4-tolylcarbamic acid esters is advantageously determined by preliminary experiments. The same would hold for nitric acid concentrations between 60 and 100% by weight to obtain the most favorable molar ratio of nitric acid to p-acetylaminotoluene.

For example, the molar ratio of 98% strength by weight nitric acid to 4-tolylcarbamic acid ester is 1.6–5:1, preferably 1.7–4:1.

If 60% strength by weight nitric acid is used, at least 6 mols of nitric acid are employed per mol of p-acetylaminotoluene. The amount of 60% strength by weight nitric acie employed per mol of p-acetylaminotoluene is preferably 6 to 12 mols, and particularly preferably 6.5 to 8 mols.

For example, the molar ratio of 98% strength by weight nitric acid, which is preferably employed in the process according to the invention, to p-acetylaminotoluene is 2.2 to 6.5:1, preferably 2.4 to 5:1.

Preferably, halogenated aliphatic hydrocarbons with 1 to 6, preferably 1 to 3, carbon atoms are employed as inert, water-immiscible organic solvent and/or diluent in the process according to the invention. The hydrocarbons can be monosubstituted or polysubstituted by fluorine, chlorine or bromine, preferably by fluorine or chlorine. The following halogenated aliphatic hydrocarbons may be mentioned by way of example: chloroform, 1,1-dichloroethane, 1,2-dichloroethane, 1,1,1-trichloroethane, methylene chloride, 1,1,-dichloropropane, 2,2-dichloropropane and monofluorotrichloromethane. Methylene chloride is particularly preferred.

The inert organic solvents and/or diluents may be employed either individually or as mixtures with one another.

The amount of the inert organic solvent and/or diluent or mixture thereof is not critical and can vary within wide ranges. In general, the amount of inert organic solvents and/or diluents is about 400 to about 2,500 ml per mol of starting material. Preferably 450 to 2,000 ml, particularly preferentially 500 to 1,500 ml, of inert organic solvent and/or diluent are employed per mol of starting material. The amount of inert organic solvent and/or diluent when 4-tolylcarbamic acid ester is the starting material is about 400 to about 2,000 ml per mol, preferably 450 to 1,000 ml per mol and more preferably 500 to 800 ml per mol of 4-tolylcarbamic acid ester. When p-acetylaminotoluene is the starting material, the inert organic solvent and/or diluent can range from 400 to 2,000 ml per mol of p-acetylaminotoluene, preferably 450 to 800 ml per mol and more particularly from 500 to 700 ml per mol.

The process according to the invention may be carried out in the presence of nitrous acid and/or substances which form nitrous acid.

As substances which form nitrous acid, the alkali metal salts and/or alkaline earth metal salts of nitrous acid, such as sodium nitrite, potassium nitrite or barium nitrite, and/or the anhydride of nitrous acid and/or nitrous fumes, such as nitrogen monoxide, dinitrogen trioxide and dinitrogen tetroxide, and/or nitrosylsulphuric acid, may be added in carrying out the nitration according to the invention. Preferably, the alkali metal salts of nitrous acid, and particularly preferentially sodium nitrite, are added.

The amount of the optionally added nitrous acid and/or substances which form nitrous acid is in general 0.01 to 5 mol %, preferably 0.03 to 4 mol %, particularly preferentially 0.05 to 3 mol %, relative to starting material employed.

As a water-binding agent, phosphorus pentoxide is preferably added to the reaction mixture. In general, about 0.25 to 1 mol, preferably 0.3 to 0.5 mol, particularly preferentially 0.32 to 0.36 mol, of phosphorus pentoxide are added per mol of starting material employed.

The process according to the invention can be carried out at temperatures of about 0° C. to about 80° C., preferably at 5° C. to 50° C., particularly preferentially at 10° C. to 40° C. and more particularly preferred at 10° C. to 25° C. In a very particular or preferred procedure, the reaction is carried out under reflux conditions and under normal pressure. When 4-tolylcarbamic acid esters are employed as the starting material, nitration can be carried out at about −10° C. to about +45° C., preferably 0° to 40° C., particularly preferentially at 10° to 25° C. When p-acetylaminotoluene is used as the starting material, nitration can be conducted at 0° to 80° C., and preferably at 20° to 50° C., and more preferably at 30° to 40° C.

In the stated temperature range, the process according to the invention can be carried out either under normal pressure or under reduced or elevated pressure, for example, at pressures in the range from about 0.2 to about 3.5 bar, preferably at 0.25 to 1.4 bar, particularly preferentially at 0.3 to 1 bar. When 4-tolylcarbamic acid esters are employed as starting materials, the pressure can be in the range of about 0.02 to 1.2 bar, preferably at 0.05 to 1 bar. When p-acetylamino toluene is used as the starting material, nitration can be conducted at pressures in the range of 0.3 to 3.5 bars, preferably 0.4 to 1.4 bar and particularly preferably 0.6 to 1 bar.

The reaction time of the nitration depends, at a constant temperature, essentially on the concentration of nitric acid and on the amount of nitric acid employed. The more concentrated the nitric acid and the greater the excess of nitric acid, relative to the starting material, the shorter is the reaction time. In general, the reaction times are about 15 minutes to about 10 hours. When 4-tolylcarbamic acid esters or p-acetylaminotoluene are employed as starting materials the reaction times are between about 15 minutes and about 3 hours.

The process according to the invention is in general conducted by simultaneously metering the starting material and the nitric acid, within the temperature range described above, into a reaction vessel containing an inert organic solvent and/or diluent, e.g., methylene chloride, which optionally contains a part of the nitric acid required for the nitration and optionally also contains additives such as nitrous acid and/or its salts and/or its anhydride and/or nitrous fumes and/or nitrosylsulphuric acid and optionally also a dehydrating agent, such as phosphorus pentoxide. In general, it is not necessary to cool the reaction mixture since the heat of reaction can be removed by the boiling inert organic solvent and/or diluent, e.g., methylene chloride. The starting material can be employed as a solution or suspension in the inert organic solvent/or diluent, e.g. methylene chloride. It is, of course, also possible to employ the starting material in the solid form or as a melt in the process according to the invention. In the case of basic starting materials it is also possible to employ these as salts of nitric acid, which can be obtained by adding about 98% strength nitric acid, for example, in methylene chloride.

When using relatively highly concentrated nitric acid it can be advantageous to introduce a mixture of nitric acid and the inert organic solvent and/or diluent, e.g., methylene chloride, synchronously with the starting material, preferably with the starting material in a suspension or solution. In that case, the quality of the desired nitroaminobenzene is further improved.

The amount of nitric acid initially introduced with the inert organic solvent and/or diluent, e.g., methylene chloride can vary within wide limits. In general, the amount of nitric acid initially introduced is about 1 to 70% by weight, preferably 2 to 50% by weight, particularly preferential 5 to 40% by weight, of the total amount required for the nitration. When 4-tolylcarbamic acid ester is used as a starting material, the amount of initially introduced nitric acid is about 1 to 70%, preferably 2 to 50%, particularly preferentially 5 to 40% of the total amount required for nitration. When p-acetylaminotoluene is used as a starting material, the amount of initially introduced nitric acid is about 1 to 80%, preferably 2 to 60% and particularly preferably 5 to 50% of the total amount required for nitration.

The abovementioned additions of nitrous acid and of substances which form nitrous acid can also be added to the nitric acid which is to be metered in, or be added simultaneously with the starting material and the nitric acid. The time period for the addition of the starting material and of the nitric acid depends on the heat of reaction which is to be removed and, in the case of a discontinuous process, is usually about 0.5 to 10 hours, preferably 2 to 5 hours, depending on the batch size.

The amount of the abovementioned additives, which can also be added to the nitric acid to be introduced into the initial charge, is in general 0.01 to 5 mols%, preferably 0.03 to 1 mol%, particularly preferentially 0.05 to 0.5 mol%, relative to the starting material employed. When p-acetylaminotoluene is employed, the amount of the abovementioned additives, which can be added to the nitric acid to be metered in is in general 0.01 to 5 mol%, preferably 0.05 to 1 mol % and particularly preferably 0.075 to 0.5 mol% relative to the p-acetylaminotoluene used.

It is, of course, also possible to take the starting material, dissolved or suspended in the inert organic solvent and/or diluent, e.g., methylene chloride and simultaneously add nitric acid, which is optionally mixed with the inert organic solvent and/or diluent, e.g., methylene chloride. This procedure is, however, less preferred than the procedures described above.

In addition to the discontinuous procedures described above, it is also possible to carry out the process according to the invention continuously. This is advantageously done with recycling or circulation of partially or completely reacted nitration mixture, for example in a loop reactor.

The nitration mixture can be worked up by adding the reaction mixture to an aqueous, about 1 to 25% strength by weight (data in % by weight relate to the content of free base after neutralization of the excess nitric acid), preferably of about 5 to 25%, more preferably 10 to 20% strength by weight, solution or suspension of an ammonium, alkali metal and/or alkaline earth metal hydroxide and/or carbonate, preferably to an aqueous alkali metal hydroxide solution, particularly preferentially to an aqueous sodium hydroxide solution. The temperature is preferably selected to be such (for example 42° to 70° C., or 50° to 95° C. when 4-tolylcarbamic acid ester is the starting material and 50° to 70° C. when p-acetylaminotoluene is the starting material) that the inert organic solvent and/or diluent, e.g., methylene chloride, distils off, if appropriate together with water. Alkaline splitting off of the protective group (such alkaline splitting off of the protective group is ruled out for aminobenzenes whose amino group is protected by an alkylsulphonyl or an arylsulphonyl radical) is preferably carried out, or completed, at about 70° to 100° C., especially at 75° to 95° C. In some cases, for example in the case of the ureas, it can also be advantageous to effect the alkaline cleavage under pressure in the temperature range of 100° to 150° C., preferably at 100° to 130° C. When 4-tolylcarbamic acid ester or p-acetylaminotoluene is employed as a starting material, the subsequent alkaline splitting off is carried out at about 80° to 100° C., preferably 90° to 95° C.

After the cleavage, the reaction product is isolated in the usual manner at about 0° to 85° C. (0° to 80° C. for 4-tolylcarbamic acid or p-acetylaminotoluene as the starting material), preferably 40° to 80° C. (50° to 70° C. for 4-tolylcarbamic acid or p-acetylaminotoluene as the starting material), for example by filtration or phase separation.

The alkaline splitting off of the protective groups can also be carried out in an aqueous/alcoholic system, or in an alcoholic system, instead of in an aqueous system.

Suitable alcohols to use for this purpose are preferably aliphatic alcohols with 1 to 4 carbon atoms, which during or after splitting off of the protective group can be distilled off together with water. Preferably, methanol, ethanol, n-propanol, isopropanol and tert.-butanol, particularly preferentially methanol, are employed for the cleavage.

It can be advantageous, instead of adding the reaction mixture to an alkaline aqueous, aqueous/alcoholic or alcoholic solution or suspension, first to neutralize the excess nitric acid, present in the reaction mixture, completely or partially, preferably completely, with a base, preferably with ammonia, ammonium hydroxide or an alkali metal hydroxide, particularly preferentially with sodium hydroxide, then to distil off the inert organic solvent and/or diluent, e.g., methylene chloride, in the presence of water, and to add a base, preferably sodium hydroxide solution, optionally together with an alcohol, to the residual aqueous suspension or emulsion, optionally after intermediate isolation of the protected nitroaminobenzenes, so as to split off the protective group, after which the mixture is worked up as described above.

Using the process according to the invention, the preferred method of working up the nitration mixture is to remove the excess nitric acid completely or partially from the nitration mixture, if appropriate after addition of water, by phase separation and/or by extraction with water, the nitric acid optionally first being neutralized.

Preferably, the excess nitric acid (which may contain a small amount of diazonium salts) is extracted discontinuously or continuously, to the extent of more than 95%, preferably more than 98%, with as little water as possible. In this way, an aqueous nitric acid solution is obtained, from which a nitric acid of about 55 to 68% strength by weight can be recovered by known industrial processes, for example by distillation.

Furthermore it is possible to remove the excess nitric acid only partially, for example to the extent of about 50 to 95%, by phase separation, if appropriate after addition of water, and/or by extraction with water. In addition to requiring little technical effort, this process variant has the advantage, especially in the case of nitroaminobenzenes which are sparingly soluble in the inert organic solvent and/or diluent, e.g., methylene chloride, and are protected at the nitrogen, that the solubility of the nitrated starting compounds in the inert organic solvent and/or diluent, e.g., methylene chloride, is increased by the nitric acid which remains.

To remove the excess nitric acid from the nitration mixture it can furthermore be advantageous first to neutralize the nitric acid partially or completely with ammonia or with an aqueous solution of an ammonium hydroxide or alkali metal hydroxide, preferably with an aqueous alkali metal hydroxide solution, particularly preferentially with aqueous sodium hydroxide solution, and to separate off the nitrate formed, if appropriate after addition of water, by a subsequent phase separation.

The further working up of the extracted reaction mixture can, in the process according to the invention, be carried out by splitting off the protective group of the nitrated aminobenzene under acid or alkaline conditions, if appropriate after first removing the inert organic solvent and/or diluent, e.g., methylene chloride.

According to a preferred embodiment, the amino protective group is split off in hydrochloric acid solution or sulphuric acid solution, particularly preferentially in sulphuric acid solution. For this, the procedure preferably followed is that in order to split off the amino protective group the product mixture obtained after the extraction is added to an aqueous sulphuric acid solution whose concentration is selected, in a manner which is in itself known, as a function of the protective group which is to be split off. In general, the concentration of the sulphuric acid is about 1 to 85% by weight, preferably 5 to 80% by weight. The temperature of the aqueous sulphuric acid to which the product is added is preferably chosen to be such that the inert organic solvent and/or diluent, e.g. methylene chloride, distils off together with water. In general, the temperatures are about 45° to 70° C.

The temperatures at which the protective group of the amino compounds are usually split off are about 60° to 100° C., preferably 70° to 95° C.

If the excess nitric acid has not been removed completely from the inert organic solvent and/or diluent, e.g., methylene chloride, it can be advantageous to add, to the aqueous sulphuric acid initially taken, substances which are capable of binding or destroying nitrous acid. For example, urea and/or amidosulphonic acid can be added. Preferably, about 0.005 to about 0.15 mol, particularly preferentially 0.01 to 0.1 mol, of urea and/or amidosulphonic acid is added per mol of starting material employed.

After the protective group has been split off, the reaction product is isolated by filtration or phase separation, in the customary manner, if appropriate after clarifying the acid solution, containing the reaction product, with active charcoal and/or if appropriate after dilution of the acid solution or suspension with water and/or if appropriate after buffering the acid solution or suspension with ammonia or with an aqueous solution of an ammonium hydroxide or alkali metal hydroxide, preferably with an aqueous alkali metal hydroxide solution, particularly preferentially with aqueous sodium hydroxide, at about 0° to 60° C., preferably at 15° to 45° C.

Instead of carrying out the acid splitting off of the amino protective group in an aqueous system, it can also be advantageous to effect the splitting off, as described above, in an aqueous/alcoholic system or in an alcoholic system.

If the splitting off of the protective group is carried out in an alkaline medium (the alkaline splitting off of the protective group is ruled out for aminobenzenes whose amino group is protected by an alkylsulphonyl or arylsulphonyl radical), the procedure followed is, for example, that the inert organic solvent and/or diluent, e.g., methylene chloride, which has been completely or partially freed from excess nitric acid by extraction and which contains the nitrated starting material in suspension or, preferably, in solution, is added to an aqueous, aqueous/alcoholic or alcoholic solution or suspension, of about 1 to 25% strength by weight, preferably 5 to 20% strength by weight (the data in % by weight relate to the content of free base after neutralization of the excess nitric acid) of an ammonium, alkali metal and/or alkaline earth metal hydroxide and/or carbonate, preferably to an aqueous alkali metal hydroxide solution, particularly preferentially to an aqueous sodium hydroxide solution, and the mixture is worked up further as described above.

In some cases, such as in the case of the nitration of 2-acetylaminoanisole, which, using the process according to the invention, admittedly gives a high para-selectivity, but in which meta-nitration cannot be completely suppressed, it can be advantageous to cleave the resulting 5-nitro- and 4-nitro-2-acetylaminoanisole mixture in an alkaline medium, as described above. This procedure gives higher yields of 5-nitro-2-aminoanisole and more colourless products than does the acid cleavage. If an even purer 5-nitro-2-aminoanisole is desired, this can be prepared by a subsequent cleavage in an acid medium.

In the process according to the invention it is of course also possible to add the reaction mixture to water after completion of the nitration, without first removing the excess nitric acid or after complete or partial neutralization of the excess nitric acid, then to remove inert organic solvent and/or diluent, e.g., methylene chloride, in a manner which is in itself known, and to isolate the protected nitroaminobenzene from the aqueous suspension or emulsion by filtration or phase separation.

Preferably, the reaction mixture, after completion of nitration and subsequent complete or partial removal of the excess nitric acid by extraction with water, is added to water, if appropriate after first neutralizing the nitric acid or after phase separation. Thereafter, the mixture is worked up as described in the preceding paragraph.

It is, of course, also possible to isolate the nitrated material from the nitration mixture, after the latter has been freed completely of excess nitric acid by extraction or neutralization described above, by distilling off the inert organic solvent and/or diluent.

This isolated solid product can be worked up, as described above, in the aqueous, aqueous/alcoholic or alcoholic system.

Furthermore, it can be advantageous to carry out a steam distillation, under normal pressure or reduced pressure, during the alkaline cleavage.

After alkaline cleavage has taken place, it can also be advantageous to separate off the cleaved product by, for example, a liquid phase separation, preferably under pressure, or to take it up in a suitable water-immiscible organic solvent, such as methylene chloride, chlorobenzene, dichlorobenzene or toluene, either at room temperature or at an elevated temperature (30° to 130° C.), separate off the organic phase, wash it with water until free from alkali, and then isolate the nitrated product, for example, by crystallization or by distillation.

Should it be necessary, the nitroaminobenzenes obtained can be purified yet further, either by recrystallization or by sublimation or by distillation.

Compared to the processes according to the prior art, the processes according to the invention offer substantial advantages. Thus, a higher yield and a higher product quality (purity) is achieved in the process according to the invention.

Furthermore, in the process according to the invention the use of additional mineral acids, such as sulphuric acid, as solvents or diluents is completely dispensed with. This not only results in a cost-reducing saving of mineral acid compared to the prior art, but at the same time solves the problems which otherwise are associated with the working up or removal of such acids. Furthermore, in the process according to the invention, the recovery of the excess nitric acid and of the inert organic solvent and/or diluent, e.g., methylene chloride, employed can be carried out simply and hence extremely economically.

A further advantage of the process according to the invention is to be seen in the fact that the nitration can be carried out technically safely, without complication, even for sizable batches. Furthermore, it is surprising that in contrast to the previously known solvent nitration processes, the yields and qualities of the isolated nitroaminobenzenes, or of the optionally intermediately isolated nitrogen-protected nitroaminobenzenes, in the process according to the invention do not decline with increasing period of metering-in of the starting products, such as becomes necessary in the case of sizable batches, because of the removal of the heat of reaction which is generated.

It is surprising, in the process according to the invention, that when 4-tolylcarbamic acid ester is the starting material, it undergoes complete nitration even when using dilute nitric acid under mild reaction conditions.

A particular advantage of the process according to the invention is that, starting from 4-tolylcarbamic acid esters, the effluent obtained after the alkaline splitting off of the protective groups contains substantially less organic material compared to the processes according to the prior art, since the alcohol formed can easily be recovered and the carbon dioxide formed at the same time is converted by the sodium hydroxide into the carbonate and hence does not require any BOD (biological oxygen demand) consumption.

Furthermore, it is very surprising that in the process according to the invention no complications as a result of the formation of diazonium salts arise. Such a phenomenon would in fact, as described in DE-AS (German Published Specification) 2,226,405, virtually rule out industrial implementation of the process according to the invention, because of the dangerous nature of the solid diazonium nitrate.

The nitroaminobenzenes are valuable intermediate products for the preparation of dyestuffs, plant protection agents, pharmaceuticals, plastics and explosives (see Ullmanns Enzyklopädie der technischen Chemie (Ullmanns Encyclopaedia of Industrial Chemistry), 4th edition, Volume 17, page 383 (1979)) and can furthermore also be employed in the dyeing of fur and of hair (see Ullmanns Enzyklopädie der technischen Chemie (Ullmanns Encyclopaedia of Industrial Chemistry), 3rd edition, Volume 12, page 767 (1960)).

The yield of nitroaminobenzenes after carrying out the process according to the invention is up to 96% of theory, and purities of up to 99.9% can be achieved.

The examples which follow are intended to illustrate the process according to the invention without, however, restricting it to these examples.

EXAMPLE 1

2,600 ml of methylene chloride, 25.7 g of 98% strength (0.4 mol) nitric acid and 9.2 g of 30% strength (0.04 mol) aqueous sodium nitrite solution are introduced into a 4 l four-necked flask equipped with a stirrer, reflux condenser, thermometer and two dropping funnels, of which one can be heated; the contents of the flask are heated to the boil under normal pressure and 231.4 g of 98% strength (3.6 mols) nitric acid and 332 g (2 mols) of 99.5% strength technical-grade 2-acetylaminoanisole, as a melt, are added dropwise, simultaneously, in the course of 3 hours. After completion of the dropwise addition, the mixture is heated under reflux for a further 30 minutes and 200 ml of water are added to the resulting solution. The phases are separated at 20° C. and the methylene chloride phase is then run at about 50°–60° C., whilst stirring, into dilute sulphuric acid, consisting of 1,764 ml of water and 196 g of 100% strength (2 mols) sulphuric acid, which additionally contains 9.7 g (0.1 mol) of amidosulphuric acid, in the course of which methylene chloride distils off together with some water. The temperature is then raised to 95° C. and is kept thereat for 2 hours, in the course of which the acetylamino group is hydrolysed to the amino group. 1.960 ml of water are then added, the mixture is cooled to 40° C. and stirred for a further 45 minutes at 40° C. and the product is filtered out and washed with water until free from acid. The moist product is dried to constant weight in vacuo at 60° to 70° C.

Yield: 272.6 g of dry product (80.6% of theory): purity: 99.4% strength 5-nitro-2-aminoanisole.

EXAMPLE 2

The procedure followed was as in Example 1, but 1,200 ml of methylene chloride and 23.1 g of 98% strength (0.36 mol) nitric acid were initially introduced with the sodium nitrite, 208.3 g of 98% strength (3.24 mols) of nitric acid were then metered in simultaneously with the melt, and the phase separation was carried out at 30° to 35° C.

Yield: 270.5 g of dry product (79.6% of theory); purity: 99.0% strength 5-nitro-2-aminoanisole.

EXAMPLE 3

The procedure followed was as in Example 1, but 1,900 ml of methylene chloride and 59.7 g of 67.5% strength (0.64 mol) nitric acid were initially introduced with the sodium nitrite at 20° C., and 537.3 g of 67.5% strength (5.76 mols) nitric acid were then metered in simultaneously with the melt, whilst keeping the reaction temperature at 20° C. by external cooling. After completion of the dropwise addition, the mixture was stirred for a further 30 minutes at 20° C., and 6 ml of water were added to the resulting solution at 20° C. to effect phase separation.

Yield: 268.0 g of dry product (79.1% of theory); purity: 99.3% strength 5-nitro-2-aminoanisole.

EXAMPLE 4

1,800 ml of methylene chloride, 23.1 g of 98% strength (0.36 mol) nitric acid and 9.2 g of 30% strength (0.04 mol) aqueous sodium nitrite solution are introduced into a 4 l four-necked flask equipped with a stirrer, reflux condenser, thermometer and two dropping funnels, of which one can be heated: the contents of the flask are heated to the boil under normal pressure and 208.3 g of 98% strength (3.24 mols) nitric acid and 332 g (2 mols) of 99.5% strength technical-grade 2-acetylaminoanisole, as a melt, are added dropwise, simultaneously, in the course of 3 hours. After completion of the dropwise addition, the mixture is heated under reflux for a further 30 minutes and 200 ml of water are added to the resulting solution. The phases are separated at 30° to 35° C. and thereafter the lower, methylene chloride, phase, at 30° to 35° C., is extracted twice more with 100 ml at a time of water which is also at 30° to 35° C. After completion of the extraction the methylene chloride phase is worked up further as described in Example 1.

Yield: 270.3 g of dry product (80.1% of theory); purity: 99.7% strength 5-nitro-2-aminoanisole.

EXAMPLE 5

The procedure followed was as in Example 1, but instead of 2,600 ml, 1,800 ml of methylene chloride were initially introduced. After completion of the dropwise addition, the mixture is heated for a further 30 minutes after reflux, the resulting solution is brought to pH 5, whilst under reflux, with a 45% strength aqueous sodium hydroxide solution, and 300 ml of water are added to the reaction mixture. The phases are separated at 30° to 35° C. and the methylene chloride phase is then allowed to run, at about 50° to 60° C., into stirred dilute sulphuric acid, consisting of 784 ml of water and 196 g of 100% strength (2 mols) sulphuric acid, which additionally contains 9.7 g (0.1 mol) of amidosulphonic acid, during which addition methylene chloride distils off with some water. The temperature is then raised to 95° C. and maintained for 2 hours, during which the acetylamino group hydrolyses to the amino group. 2,940 ml of water are then added, the mixture is cooled to 40° C. and is stirred for a further 45 minutes at 40° C., and the product is filtered off and washed with water until free from acid. The moist product is dried to constant weight in vacuo at 60° to 70° C.

Yield: 273.9 g of dry product (80.9% of theory); purity: 99.3% strength 5-nitro-2-aminoanisole.

EXAMPLE 6

The procedure followed was as in Example 5, but no amidosulphonic acid was added to the dilute sulphuric acid. The yield and purity of the product were virtually the same as in Example 5.

EXAMPLE 7

1,200 ml of methylene chloride, 34.7 g of 80% strength (0.44 mol) nitric acid and 9.2 g of 30% strength (0.04 mol) aqueous sodium nitrite solution are introduced into a 2 l four-necked flask equipped with a stirrer, reflux condenser, thermometer and two dropping funnels, of which one can be heated: the contents of the flask are heated to the boil under normal pressure and 311.8 g of 80% strength (3.96 mol) nitric acid and 332.3 g (2 mols) of 99.4% strength technical-grade 2-acetylaminoanisole, as a melt, are added dropwise, simultaneously, in the course of 3 hours. After completion of the dropwise addition, the mixture is heated under reflux for a further 30 minutes, 200 ml of water are added to the resulting solution, this reaction mixture is added to 731 ml of water and the pH is then brought to 5 with a 45% strength aqueous sodium hydroxide solution at about 20° C. Thereafter, the methylene chloride is next removed by distillation at a bottom temperature of about 50° C., which at the end is raised to 95° C., the residue is cooled to 40° C. and stirred for a further 30 minutes at 40° C. and the product is filtered off and rinsed twice with water. The moist product is dried to constant weight in vacuo at 60° to 70° C.

Yield: Dry product 413.2 g of crude product.

This crude product is introduced into dilute sulphuric acid consisting of 784 ml of water and 196 g of 100% strength (2 mols) sulphuric acid. the mixture is heated to 95° C. and this temperature is maintained for 3 hours, during which the acetylamino group hydrolyses to the amino group. Thereafter, the procedure is continued as described in Example 5.

Yield: 278.3 g (82.1% of theory) of dry product; purity: 99.2% strength 5-nitro-2-aminoanisole.

EXAMPLE 8

1,400 ml of methylene chloride, 23.1 g of 98% strength (0.36 mol) nitric acid and 9.2 g of 30% strength (0.04 mol) of aqueous sodium nitrite solution are introduced into a 4 l four-necked flask equipped with a stirrer, reflux condenser, thermometer and two dropping funnels, of which one can be heated; the contents of the flask are heated to the boil under normal pressure and 208.3 g of 98% strength (3.24 mols) nitric acid and 332.3 g (2 mols) of 99.4% strength technicalgrade 2-acetylaminoanisole, as a melt, are added dropwise, simultaneously, in the course of 3 hours. After completion of the dropwise addition, the mixture is heated for a further 30 minutes under reflux, a slurry of 20.5 g of bleaching earth in 200 ml of water is added to the resulting solution, the mixture is then heated under reflux for a further 30 minutes and filtered hot, the filter residue is additionally rinsed once with about 50 ml of methylene chloride, and the phases are separated at 30° to 35° C. The methylene chloride phase is allowed to run into 1,000 ml of stirred water and the pH is then brought to 5 with a 45% strength aqueous sodium hydroxide solution, at about 20° to 30° C. Thereafter, the procedure is continued as described in Example 7.

Yield: Dry product 401.5 g of crude product; yield: Dry product 271.5 g (80.5% of theory); purity: 99.7% strength 5-nitro-2-aminoanisole.

EXAMPLE 9

The procedure followed was as in Example 2, but after the phase separation at 30° to 35° C. the methylene chloride phase is allowed to run, at about 45° C., into dilute stirred sodium hydroxide solution consisting of 2,280 ml of water and 145.6 g (3.64 mols) of NaOH, during which methylene chloride distils off together with some water. The temperature is then raised to 80° C., the residual methylene chloride is removed under reduced pressure and the temperature of 80° C. is maintained for 2 hours, during which the acetylamino group of the 5-nitro-2-acetylaminoanisole hydrolyses completely to the amino group. The product is filtered off at 80° C. and washed with water until free from alkali. The moist product is dried to constant weight in vacuo at 60° to 70° C.

Yield: 314.6 g of dry product (83.1% of theory). Purity: 88.8% strength 5-nitro-2-aminoanisole, which still contains about 8.5% of 4-nitro-2-acetylaminoanisole and about 2.5% of 4-nitro-2-aminoanisole.

EXAMPLE 10

The procedure followed was as in Example 9, but the moist product, after having been washed with water until free from alkali, is resuspended in about 800 ml of 5% strength by weight sulphuric acid on the suction filter, and is filtered off and washed with water until free from acid. The moist product is dried to constant weight in vacuo at 60° to 70° C.

Yield: 299.2 g of dry product (82.6% of theory). Purity: 92.8% strength 5-nitro-2-aminoanisole, which still contains about 7% of 4-nitro-2-acetylaminoanisole and about 0.1% of 4-nitro-2-aminoanisole.

EXAMPLE 11

The procedure followed was as in Example 9, but the product obtained was subsequently introduced, at about 60° C., into dilute sulphuric acid, consisting of 2,979 ml of water and 156.8 g of 100% strength (1.6 mols) sulphuric acid, the mixture was heated to 95° C. and the temperature was maintained for 2.5 hours. The mixture is then cooled to 40° C. and stirred for a further 45 minutes at 40° C., and the product is filtered off and washed with water until free from acid. The moist product is dried to constant weight in vacuo at 60° to 70° C.

Yield: 271.7 g of dry product (80.7% of theory). Purity: 99.9% strength 5-nitro-2-aminoanisole.

EXAMPLE 12

1,200 ml of methylene chloride, 7.7 g of 98% strength (0.12 mol) nitric acid and 4.6 g of 30% strength (0.02 mol) aqueous sodium nitrite solution are introduced into a 2 l four-necked flask equipped with a stirrer, reflux condenser, thermometer and two dropping funnels, of which one can be heated: the contents of the flask are heated to the boil under normal pressure and 146.6 g of 98% strength (2.28 mols) nitric acid and 334.1 g (2 mols) of 98.9% strength technical-grade 4-acetylaminoanisole, as a melt, are added dropwise, simultaneously, in the course of 3 hours. After completion of the dropwise addition, the mixture is heated under reflux for a further 30 minutes and the solution obtained is allowed to run, at 50° to 60° C., into stirred sodium hydroxide solution, consisting of 792 ml of water and 104 g (2.6 mols) of NaOH, in the course of which methylene chloride distils off with some water. The temperature is then raised to 95° C. and maintained thereat for 45 minutes, in the course of which the acetylamino group of the 3-nitro-4-acetylaminoanisole hydrolyses completely to the amino group. The mixture is cooled to 50° C. and stirred for a further hour at 50° C., and the product is filtered off, washed with water until free from alkali and then sucked dry thoroughly for about 0.5 hour.

Yield: 356.5 g of moist product (96.1% of theory); content: 90.7% strength 3-nitro-4-aminoanisole.

After drying the moist product to constant weight in vacuo at 60° to 70° C., the product has a purity of 99.1%.

EXAMPLE 13

The procedure followed was as in Example 12, but after completion of the dropwise addition, and after a subsequent 30 minutes of stirring under reflux, 200 ml of water are added to the solution obtained. The phases were separated at 30° to 35° C. The lower, methylene chloride, phase is allowed to run, at 50° to 60° C., into stirred dilute sodium hydroxide solution, consisting of 1,672 ml of water and 92 g (2.3 mols) of NaOH, in the course of which methylene chloride distils off together with some water. The temperature is then raised to 95° C. and maintained for 30 minutes. Thereafter, the procedure was continued as in Example 12.

Yield: 346.0 g of moist product (95.2% of theory); content: 92.5% strength 3-nitro-4-aminoanisole.

After drying the moist product to constant weight in vacuo at 60° to 70° C., the product has a purity of 99.7%.

EXAMPLE 14

The procedure followed was as in Example 12, but instead of 4.6 g, 2.3 g of a 30% strength (0.01 mol) aqueous sodium nitrite solution were initially introduced. After completion of the dropwise addition, and after 30 minutes' subsequent stirring under reflux, 200 ml of water are added to the solution obtained. The phases are separated at 30° to 35° C., and the lower, methylene chloride, phase is then run, at about 50° to 60° C., into stirred dilute sulphuric acid, consisting of 1,764 ml of water and 196 g of 100% strength (2 mols) sulphuric acid, which additionally contains 9.7 g (0.1 mol) of amidosulphonic acid, in the course of which methylene chloride distils off with some water. The temperature is then raised to 95° C. and maintained for 3.5 hours, in the course of which the acetylamino group hydrolyses to the amino group. Thereafter, 1,960 ml of water are added, the mixture is cooled to 40° C. and stirred for a further hour at 40° C., and the product is filtered off and washed with water until free from acid. The moist product is dried to constant weight in vacuo at 60° to 70° C. Yield: 312.5 g of dry product (92.4% of theory). Purity: 99.4% strength 3-nitro-4-aminoanisole.

By raising the pH value of the mother liquor to pH 5 with gaseous ammonia and then filtering at 20° C., a further 2% of theory of 3-nitro-4-aminoanisole can be isolated.

EXAMPLE 15

1,400 ml of methylene chloride and 28.3 g of 98% strength (0.44 mol) nitric acid are introduced into a 4 l four-necked flask equipped with a stirrer, reflux condenser, thermometer and two dropping funnels, the contents of the flask are heated to the boil under normal pressure and 254.6 g of 98% strength (3.96 mols) nitric acid and 329.3 g (2 mols) of 99% strength technical-grade 2,4-dimethylacetanilide dissolved in 1,200 ml of methylene chloride are added dropwise, simultaneously, in the course of 3 hours. After completion of the dropwise addition, the mixture is heated under reflux for a further 30 minutes and 200 ml of water are added to the resulting solution. The phases are separated at 30° to 35° C., and thereafter the methylene chloride phase is run, at about 50° to 60° C., into stirred dilute sodium hydroxide solution, consisting of 793 ml of water and 304 g (7.6 mols) of NaOH, in the course of which methylene chloride distils off with some water. The temperature is then raised to 80° C., the residual methylene chloride is removed under reduced pressure, 793 g of methanol are added, again at 80° C., and the mixture is heated under reflux for 3.75 hours, in the course of which the acetylamino group hydrolyses to the amino group. The mixture is then cooled to 25° C. and stirred for a further 0.5 hour at 25° C., and the product is filtered off and washed with water until free from alkali. The moist product is dried to constant weight in vacuo at 50° to 55° C.

Yield: 278.3 g of dry product (83.3% of theory). Purity: 99.5% strength 4,6-dimethyl-2-nitroaniline.

EXAMPLE 16

694 ml of methylene chloride, 14.8 g of 98% strength (0.23 mol) nitric acid and 2.7 g of 30% strength (0.0117 mol) aqueous sodium nitrite solution are introduced into a 2 l four-necked flask equipped with a stirrer, reflux condenser, thermometer and two dropping funnels, the contents of the flask are heated to the boil under normal pressure and 134.4 g of 98% strength (2.09 mols) nitric acid and 309.9 g (1.16 mols) of 94.8% strength N-[[2-[2-(methoxyethoxy)]-ethoxyphenyl]]-acetamide are added dropwise, simultaneously, in the course of 2 hours. After completion of the dropwise addition, the mixture is heated under reflux for a further 30 minutes, 116 ml of water are added to the resulting solution, the pH is brought to 5, under reflux, with a 45% strength aqueous sodium hydroxide solution, and the mixture is cooled to 30° C. The phases are separated at 30° C. and thereafter the methylene chloride phase is run, at about 50° to 60° C., into stirred dilute sulphuric acid, consisting of 682.5 ml of water and 227.5 g of 100% strength (2.32 mols) sulphuric acid, which additionally contains 4.5 g (0.0463 mol) of amidosulphonic acid, in the course of which methylene chloride distils off with some water. The temperature is then raised to 80° C., the residual methylene chloride is removed under reduced pressure and the temperature of 80° C. is maintained for 1.25 hours, during which the acetylamino group hydrolyzes to the amino group. The mixture is then cooled to 40° C. and brought to pH 4 with 45% strength aqueous sodium hydroxide solution, whilst being cooled externally, and the upper, oily phase is separated from the sodium sulphate solution at 40° C. For precise determination of the yield, the sodium sulphate solution was extracted once with 100 ml of methylene chloride, the oily phase was taken up in methylene chloride, the combined methylene chloride solutions were dried over sodium sulphate, the methylene chloride was removed in vacuo and the oil was dried to constant weight in vacuo at 60° C.

Yield: 287.6 g of dry product (82.1% of theory). To determine the purity, a part of the product was taken up in ethyl acetate and the solution filtered through a silica gel column. The solution obtained was evaporated to constant weight in vacuo and 97.9% of the product employed were obtained.

Purity: 86.7% strength 2-[2-(2-methoxyethoxy)]-ethoxy-4-nitroaniline, which still contains 10.1% of 2,5-isomer.

If, after cleavage, the mixture is not brought to pH 4 with NaOH, but is diluted with water, and isolation is effected at 20° C. from a 5% strength by weight sulphuric acid or, after neutralization of the solution with gaseous ammonia, at pH 0.5, the products obtained have purities of 98.1 and 95.4% respectively and only contain, respectively, 0.6 and 2.2% of 2,5-isomer.

EXAMPLE 17 (repetition of Example 2 of U.S. Pat. No. 2,459,002)

The experiment was carried out in a 1 mol batch, as described in Example 2 of the U.S. patent specification, as a one-vessel process, without intermediate isolation of the 2-acetylaminoanisole, with subsequent nitration, the 5-nitro-2-acetylaminoanisole being isolated a) at 30° C. or b) at 20° C., washed with water until free from acid and dried to constant weight in vacuo at 60° C.

(a) Yield: 67.3 g of dry product (31.0% of theory). Purity: 96.9%. Melting point: 150°–153° C.

(b) Yield: 120.2 g of dry product (54.8% of theory). Purity: 95.9%. Melting point 145°–152° C.

Because of the low yields of the 5-nitro-2-acetylaminoanisole isolated as an intermediate, the subsequent desacetylation was not carried out.

EXAMPLE 18 (repetition of Example 2 of U.S. Pat. No. 2,459,002)

The experiment was carried out in a 2 mols batch, as described in Example 2 of the U.S. patent specification, as a one-vessel process, but without intermediate isolation of the 5-nitro-2-acetylaminoanisole as described in Example 4 of the U.S. patent specification, with subsequent neutralization of the excess nitric acid with sodium carbonate, steam distillation of the chlorobenzene, desacetylation with sulphuric acid and clarification with active charcoal. The sulphuric acid solution was stirred into 5 l of ice water and the product which precipitated was filtered off, washed with water until free from acid and dried to constant weight in vacuo at 60° to 70° C.

Yield: 91.6 g of dry product (15.0% of theory). Purity: 55.1% strength 5-nitro-2-aminoanisole.

The mother liquor was neutralized with gaseous ammonia to pH 7–8 and the product which precipitated was filtered off, washed with water and dried to constant weight in vacuo at 60° to 70° C.

Yield: 132.5 g of dry product (32.9% of theory). Purity: 83.5% strength 5-nitro-2-aminoanisole.

EXAMPLE 19

100 ml of methylene chloride are introduced into a 2 l four-necked flask equipped with a stirrer, reflux condenser, thermometer and two dropping funnels, and 165.2 g (1 mol) of 4-tolylcarbamic acid methyl ester, dissolved in 500 ml of methylene chloride, and 102.9 g of 98% strength (1.6 mols) nitric acid dissolved in 200 ml of methylene chloride are added simultaneously in the course of 1 hour, at 10° C. and under normal pressure, the temperature being maintained by external cooling. After completion of the dropwise addition, the nitration mixture is allowed to come to 20° C. and is stirred for a further 1.75 hours, and the solution obtained is allowed to run, with stirring, into dilute sodium hydroxide solution, consisting of 480 ml of water and 144 g (3.6 mols) of NaOH, at 50° to 60° C., in the course of which methylene chloride distils off with a small amount of water. After the entire quantity of methylene chloride has distilled off, the temperature is raised to 95° C. and is maintained for 3 hours, whilst at the same time the methanol formed on hydrolysis of the 2-nitro-4-tolylcarbamic acid methyl ester to give the amino group is distilled off. The mixture is cooled to 60° C. and stirred for a further 30 minutes at 60° C., and the product is filtered off and washed alkali-free with water. The moist product is dried to constant weight in vacuo at 60° C. Yield: 145.4 g of dry product (94.9% of theory); purity: 99.3%.

EXAMPLE 20

100 ml of methylene chloride are introduced into a 2 l four-necked flask equipped with a stirrer, reflux condenser, thermometer and two dropping funnels, and 165.2 g (1 mol) of 4-tolylcarbamic acid methyl ester, dissolved in 400 ml of methylene chloride, and 109.3 g of 98% strength (1.7 mols) nitric acid dissolved in 150 ml of methylene chloride are added simultaneously in the course of 1 hour, at 20° C. and under normal pressure, the temperature being maintained by external cooling. After completion of the dropwise addition, the mixture is stirred for a further hour at 20° C., the resulting solution is extracted twice with 100 ml of water at a time, and the organic solvent is then distilled off. Yield: 209.3 g of crude product, of melting point 96° to 102° C. This crude product is introduced into dilute sodium hydroxide solution, consisting of 450 ml of water and 112 g (2.8 mols) of NaOH, and the mixture is heated to 95° C. and kept at this temperature for 3 hours, whilst distilling off the methanol formed during hydrolysis of the 2-nitro-4-tolylcarbamic acid methyl ester to the amino group. The mixture is cooled to 60° C. and stirred for a further 30 minutes at 60° C., and the product is filtered off and washed alkali-free with water. The moist product is dried to constant weight in vacuo at 60° C. Yield: 144.4 g of dry product (94.6% of theory); purity: 99.7%.

EXAMPLE 21

The procedure followed was as in Example 20, but the nitration mixture obtained after twice extracting with 100 ml of water at a time was, without intermediate isolation, allowed to run, with stirring, into dilute sodium hydroxide solution, consisting of 480 ml of water and 120 g (3.0 mols) of NaOH, at 50° to 60° C., and was further worked up as described in Example 19.

Yield: 144.7 g of dry product (94.9% of theory); purity: 99.8%.

EXAMPLE 22

200 ml of methylene chloride, 12.2 g of 98% strength (0.19 mol) nitric acid and 0.17 g of 40.83% strength (0.001 mol) aqueous sodium nitrite solution were initially introduced into a 2 l four-necked flask equipped with a stirrer, reflux condenser, thermometer and two dropping funnels, the mixture was heated to the boil (18° C.) under reduced pressure (400 mbar), and 165.2 g (1 mol) of 4-tolylcarbamic acid methyl ester dissolved in 400 ml of methylene chloride and 110.0 g of 98% strength (1.71 mols) nitric acid, introduced via the reflux condenser, are simultaneously added dropwise at 18° C. After completion of the dropwise addition, stirring is continued for 1 hour at the same temperature and the same pressure, the resulting solution is extracted twice with 100 ml of water at a time, and the organic solution is run, whilst stirring, into dilute sodium hydroxide solution, consisting of 480 ml of water and 120 g (3.0 mols) of NaOH, at 50° to 60° C., in the course of which methylene chloride distils off together with a small amount of water. Thereafter, working up is continued as described in Example 19.

Yield: 144.8 g of dry product (95.1% of theory); purity: 99.9%.

EXAMPLE 23

100 ml of methylene chloride are introduced into a 2 l four-necked flask equipped with a stirrer, reflux condenser, thermometer and two dropping funnels, and 179.2 g (1 mol) of 4-tolylcarbamic acid ethyl ester, dissolved in 400 ml of methylene chloride, and 109.3 g of 98% strength (1.7 mols) nitric acid dissolved in 150 ml of methylene chloride are added simultaneously in the course of 1 hour, at 20° C. and under normal pressure, the temperature being maintained by external cooling. After completion of the dropwise addition, the mixture is stirred for a further hour at 20° C., the resulting solution is extracted twice with 100 ml of water at a time, and the organic solvent is then distilled off.

Yield: 228 g of crude product, of melting point 56° to 58° C.

The solution of this crude product in 400 ml of methylene chloride is allowed to run into dilute sodium hydroxide solution, consisting of 550 ml of methanol and 100 g (2.5 mols) of NaOH, at about 40° C., and the mixture is then stirred for a further 30 minutes at the reflux temperature (42° to 48° C.), as a result of which the contents of the flask turn dark red and sodium carbonate precipitates. The methylene chloride is then distilled off under normal pressure and 1 liter of water is added to the suspension, as a result of which the sodium carbonate dissolves. The moist product is dried to constant weight in vacuo at 60° C.

Yield: 142.0 g of dry product (92.6% of theory); purity: 99.2%.

EXAMPLE 24

The procedure described in Example 23 was followed, except that the methylene chloride solution, which had twice been extracted with 100 ml of water at a time, was allowed to run, without intermediate isolation, directly into dilute sodium hydroxide solution consisting of 550 ml of methanol and 100 g (2.5 mols) of NaOH at about 40° C.

The yield and purity of the dried product was virtually the same as in Example 23.

EXAMPLE 25

(Repetition of Example 4 of U.S. Pat. No. 2,459,002).

The experiment was carried out in a 1 mol batch as described in Example 4 of the U.S. Pat. No. 2,459,002 as a one-vessel process, without intermediate isolation of the 3-nitro-4-acetylaminotoluene, and with subsequent acid cleavage.

The moist product was dried to constant weight in vacuo at 60° C.

Yield: 89.0 g of dry product (50.5% of theory); purity: 86.4%.

EXAMPLE 26 (Comparison example)

The procedure described in Example 25 was followed, but after the steam distillation 60 g (1.5 mols) of NaOH were added to the hot, aqueous and neutral suspension, and the mixture was heated to 95° C. and kept at this temperature for 1½ hours, in the course of which the acetylamino group hydrolyzes to the amino group. The mixture is cooled to 60° C. and stirred for a further ½ hour at 60° C. and the product is filtered off and washed with water until free from alkali. The moist product is dried to constant weight in vacuo at 60° C.

Yield: 134.5 g of dry product (82.4% of theory); purity: 93.2%.

EXAMPLE 27

A suspension of 298.4 g (2 mols) of 4-acetylaminotoluene and 1,200 ml of methylene chloride is heated to the boiling point under normal pressure in a 2 l three-necked flask provided with a stirrer, reflux condenser, thermometer and dropping funnel, and 308.6 g of 98% strength nitric acid (4.8 mols) are added dropwise in the course of 30 minutes, a solution forming after about half of the acid has been added. After the dropwise addition of the nitric acid, the mixture is heated under reflux for a further 50 minutes and the resulting solution is allowed to run into dilute sodium hydroxide solution, consisting of 680 ml of water and 232 g (5.8 mols) of NaCH, at 50° to 60° C., whilst stirring, methylene chloride being distilled off with 25 to 30 ml of water. When all the methylene chloride has been distilled off, the temperature is increased to 95° C. and kept at this level for 1½ hours, the acetylamino group being hydrolyzed to the amino group. The mixture is cooled to 60° C. and subsequently stirred at 60° C. for ½ hour and the precipitate is filtered off and washed with water until free from alkali.

The moist product is dried to constant weight in vacuo at 60° C.

Yield: 293.6 g of dry product (96.0% of theory), Purity: 99.5%.

EXAMPLE 28

The experiment was carried out as described in Example 27, but 298.4 g (2 mols) of technical grade 4-acetylaminotoluene which had been washed with methylene chloride was employed.

Yield: 293.7 g of dry product (96.2% of theory). Purity: 99.7%.

EXAMPLE 29

The experiment was carried out as described in Example 27, but 304.5 g of 98% strength by weight technical grade 4-acetylaminotoluene (2 mols) were employed.

Yield: 295.4 g of dry product (95.5% of theory). Purity: 98.4%.

EXAMPLE 30

A suspension of 304.5 g of 98% pure technical grade 4-acetylaminotoluene (2 mols) and 1,200 ml of methylene chloride is heated to the boiling point under normal pressure in a 2 l three-necked flask provided with a stirrer, reflux condenser, thermometer and dropping funnels.

308.6 g of 98% strength nitric acid (4.8 mols) are added dropwise through the reflux condenser in the course of 30 minutes, a solution forming after about half of the acid has been added. After the dropwise addition of the nitric acid, the mixture is heated under reflux for a further 50 minutes and the resulting solution is allowed to run into dilute sodium hydroxide solution, consisting of 589.8 ml of water and 216 g (5.4 mols) of NaOH, at 50° to 60° C., whilst stirring, methylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and is subsequently stirred at 60° C. for ½ hour and the precipitate is filtered off and washed with water until free from alkali. The moist product is dried to constant weight in vacuo at 60° C.

Yield: 294.9 g of dry product (95.7% of theory). Purity: 98.8%.

EXAMPLE 31

A suspension of 304.5 g of 98% pure technical grade 4-acetylaminotoluene (2 mols) and 1,200 ml of methylene chloride is heated to the boiling point under normal pressure in a 2 l three-necked flask provided with a stirrer, reflux condenser, thermometer and dropping funnel, and 308.6 g of 98% strength nitric acid (4.8 mols) are added dropwise in the course of 30 minutes, a solution forming after about half of the acid has been added. When the dropwise addition of the nitric acid has ended, the mixture is heated under reflux for a further 50 minutes and the resulting solution is allowed to run into dilute sodium hydroxide solution, consisting of 589.8 ml of water and 216 g (5.4 mols) of NaOH, at 50° to 60° C., whilst stirring, methylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and subsequently stirred at 60° C. for ½ hour and the precipitate is filtered off and washed with water until free from alkali. The moist product is dried to constant weight in vacuo at 60° C.

Yield: 295.2 g of dry product (95.5% of theory). Purity: 98.4%

EXAMPLE 32

A suspension of 304.5 g of 98% pure technical trade 4-acetylaminotoluene (2 mols) and 1,200 ml of methylene chloride is heated to the boiling point under normal pressure in a 2 l three-necked flask provided with a stirrer, reflux condenser, thermometer and dropping funnel.

308.6 g of 98% strength nitric acid (4.8 mols) are added dropwise through the reflux condenser in the course of 30 minutes, a solution forming after about half of the acid has been added. After the dropwise addition of the nitric acid, the mixture is heated under reflux for a further 50 minutes and the resulting solution is allowed to run into dilute sodium hydroxide solution, consisting of 680 ml of water and 232 g (5.8 mols) of NaOH, at 50° to 60° C., whilst stirring methylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and is subsequently stirred at 60° C. for ½ hour and the precipitate is filtered off and washed with water until free from alkali. The moist product is dried to constant weight in vacuo at 60° C.

Yield: 294.1 g of dry product (95.5% of theory). Purity: 98.8%.

EXAMPLE 33

The experiment was carried out as described in Example 32 but (a) 900 ml of methylene chloride, and (b) 4,000 ml of methylene chloride were employed.

Yield: 292.8 g of dry product (94.9% of theory)
Purity: 98.6%
Yield: 295.0 g of dry product (95.9% of theory)
Purity: 98.9%

EXAMPLE 34

A suspension of 304.5 g of 98% pure technical grade 4-acetylaminotoluene (2 mols) and 1,200 ml of methylene chloride is heated to the boiling point under normal pressure in a 2 l three-necked flask provided with a stirrer, reflux condenser, thermometer and dropping funnel, and a mixture of 308.6 g of 98% strength ntric acid (4.8 mols) and 308 g of methylene chloride is added dropwise in the course of 30 minutes, a solution forming after about half of the acid has been added. After the dropwise addition of the nitric acid/methylene chloride mixture, the reaction mixture is heated under reflux for a further 50 minutes and the resulting solution is allowed to run into dilute sodium hydroxide solution, consisting of 589.8 ml of water and 216 g (5.4 mols) of NaOH, at 50° to 60° C., whilst stirring, methylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and subsequently stirred at 60° C. for ½ hour and the precipitate is filtered off and washed with water until free from alkali. The moist product is dried to constant weight in vacuo at 60° C.

Yield: 295.3 g of dry product (95.8% of theory) Purity: 98.7%

EXAMPLE 35

A suspension of 298.4 g (2 mols) of 4-acetylaminotoluene and 1,200 ml of methylene chloride is heated to the boiling point under normal pressure in a 3 l three-necked flask provided with stirrers and a reflux condenser, thermometer and dropping funnel, and 570 g of 66.3% strength nitric acid (6 mols) are first added dropwise in the course of 30 minutes and 128.6 g of 98% strength nitric acid (2 mols) are added dropwise in the course of a further 30 minutes, a solution already forming during the addition of the nitric acid. After the dropwise addition of the nitric acid, the mixture is heated under reflux for a further 30 minutes and the resulting solution is allowed to run into dilute sodium hydroxide solution, consisting of 680 ml of water and 360 g (9 mols) of NaOH, at 50° to 60° C., whilst stirring, methylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and subsequently stirred at 60° C. for ½ hour and the precipitate is filtered off and washed with water until free from alkali. The moist product is dried to constant weight in vacuo at 60° C.

Yield: 284.1 g of dry product (92.4% of theory). Purity: 99.0%

EXAMPLE 36

A suspension of 298.4 g (2 mols) of 4-acetylaminotoluene and 1,200 ml of methylene chloride is heated to the boil under normal pressure in a 2 l three-necked flask provided with a stirrer, reflux condenser, thermometer and dropping funnel, and 308.6 g of 98% strength nitric acid (4.8 mols) are added dropwise in the course of 30 minutes, a solution forming after about half of the acid has been added. After the dropwise addition of the nitric acid, the mixture is heated under reflux for a further 50 minutes, 100 ml of water are added to the resulting solution, the stirrer is switched off and the two phases are separated. The lower methylene chloride phase is extracted 3 more times with 75 ml of water each time and is then allowed to run into dilute sodium hydroxide solution, consisting of 680 ml of water and 120 g (3 mols) of NaOH, at 50°-60° C., whilst stirring, ethylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and subsequently stirred at 60° C. for ½ hour and the precipitate is filtered off and washed with water until free from alkali. The moist product is dried to constant weight in vacuo at 60° C.

Yield: 288.7 g of dry product (94.8% of theory) Purity: 99.9%

The combined aqueous phases of the nitration mixture, which amount to about 540 g of an approximately 30 to 33% strength nitric acid, are heated to the boiling point and concentrated, by water and nitric acid being distilled off, to an approximately 55% strength nitric acid and then, by distillation with concentrated sulphuric acid, to an approximately 98% strength nitric acid, which is re-used in the next experiments.

EXAMPLE 37

The experiment was carried out as described in Example 36 but 298.4 g (2 mols) of technical grade 4-acetylaminotoluene which had been washed with methylene chloride were employed.

Yield: 289.8 g of dry product (95.0% of theory) Purity: 99.8%.

EXAMPLE 38

The experiment was carried out as described in Example 36, but 304.5 g of 98% strength by weight technical grade 4-acetylaminotoluene (2 mols) were employed.

Yield: 287.6 g of dry product (93.6% of theory) Purity: 99.0%

EXAMPLE 39

The procedure followed was as in Example 38 but the nitric acid was metered in through the reflux condenser.

Yield: 287.9 g of dry product (93.8% of theory) Purity: 99.1%.

EXAMPLE 40

The procedure followed was as in Examples 36, 37, 38, and 39, but the extracted methylene chloride phase was allowed to run into dilute sodium hydroxide solution consisting of 498 ml of water and 88 g (2.2 mols) of NaOH.

The yield and purity of the products was practically the same as in the corresponding Examples 36, 37, 38 and 39.

EXAMPLE 41

A suspension of 298.4 g (2 mols) of 4-acetylaminotoluene and 1,200 ml of methylene chloride is heated to the boiling point under normal pressure in a 3 l three-necked flask provided with a stirrer, reflux condenser, thermometer and dropping funnel, and 570 g of 66.3% strength nitric acid (6 mols) are first added dropwise in the course of 30 minutes, and 128.6 g of 98% strength nitric acid (2 mols) are added dropwise in the course of a further 30 minutes, a solution already forming during the addition of the nitric acid. After the dropwise addition of the nitric acid, the mixture is heated under reflux for a further 30 minutes, and the subsequent procedure is as described in Example 36.

Yield: 279.6 g of dry product (91.8% of theory) Purity: 99.8%

EXAMPLE 42

1,200 ml of methylene chloride are initially introduced into a 2 l three-necked flask provided with a stirrer, reflux condenser and thermometer and two dropping funnels, one of which can be heated, and are heated to the boiling point under normal pressure and 308.6 of 98% strength nitric acid (4.8 mols) and 304.5 g of 98% pure technical grade 4-acetylaminotoluene (2 mols), in the form of a melt, are simultaneously added dropwise in the course of 3 hours. After the dropwise addition, the mixture is heated under reflux for a further 30 minutes and the resulting solution is allowed to run into dilute sodium hydroxide solution, consisting of 680 ml of water and 232 g (5.8 mols) of NaOH, at 50° to 60° C., while stirring, methylene chloride being distilled off with 25 to 30 ml of water. When all the methylene chloride has been distilled off, the temperature is increased to 95° C. and is kept at this level for 1½ hours, the acetylamino group being hydrolyzed to the amino group. The mixture is cooled to 60° C. and is subsequently stirred at 60° C. for 30 minutes and the product is filtered off and washed with water until free from alkali. The moist product is dried to constant weight in vacuo at 60° C.

Yield: 296.75 g of dry product (96.3% of theory). Purity: 98.8%

EXAMPLE 43

1,200 ml of methylene chloride 30.9 g of 98% strength nitric acid (0.48 mol) and 0.33 g of 40.83% strength aqueous sodium nitrite solution (0.002 mol) are initially introduced into a 2 l three-necked flask provided with a stirrer, reflux condenser and thermometer and two dropping funnels, one of which can be heated, and are heated to the boiling point under normal pressure, and 277.7 g of 98% strength nitric acid (4.32 mols) and 304.5 g of 98% pure technical grade 4-acetylaminotoluene (2 mols) in the form of a melt, are simultaneously added dropwise in the course of 3 hours. After the dropwise addition, the subsequent procedure was as described in Example 42.

Yield: 295.5 g of dry product (95.9% of theory). Purity: 98.8%.

EXAMPLE 44

1,200 ml of methylene chloride, 154.3 g of 98% strength nitric acid (2.4 mols) and 0.33 g of 40.83% strength aqueous sodium nitrite solution (0.002 mol) are initially introduced into a 2 l three-necked flask provided with a stirrer, reflux condenser and thermometer and two dropping funnels, one of which can be heated, and are heated to the boiling point under normal pressure, and 154.3 g of 98% strength nitric acid (2.4 mols) and 304.5 g of 98% pure technical grade 4-acetylaminotoluene (2 mols), in the form of a melt, are simultaneously added dropwise in the course of 3 hours. After the dropwise addition, the subsequent procedure was as described in Example 42.

Yield: 296.8 g of dry product (96.0% of theory). Purity: 98.5%.

EXAMPLES 45-52

Examples 45 to 52 show the criticality of the order of addition of the para-acetylamino toluene and the nitric acid to the reaction mixture.

Successive addition of nitric acid and the aminotoluene to be nitrated may prove useful in small batches, but such addition is virtually inoperable on a large scale, especially on a commercial scale.

EXAMPLE 45

1,200 ml of methylene chloride and 304.5 g of 98% pure technical grade 4-acetylamino toluene (2 mols) are initially introduced into a 2 liter three-necked flask provided with a stirrer, reflux condenser and thermometer and a dropping funnel, and are heated to the boiling point under normal pressure, and 308.6 g (4.8 mols) of 98% strength nitric acid is added dropwise in the course of 3 hours. After the dropwise addition, the mixture is heated under reflux for a further 30 minutes and the resulting solution is allowed to run into dilute sodium hydroxide solution, consisting of 680 ml of water and 232 g (5.8 mols) of NaOH, at 50° to 60° C., while stirring, methylene chloride being distilled off with 25 to 30 ml of water. When all the methylene chloride has been distilled off, the temperature is increased to 95° C. and is kept at this level for 1½ hours, the acetylamino group being hydrolized to the amino group. The mixture is cooled to 60° C. and is subsequently stirred at 60° C. for 30 minutes and product is filtered off and washed with water until free from alkali. The moist product is dried to constant weight in vacuo at 60° C. Yield: 285.9 g (89.1% of the theoretical yield). Purity: 94.85%.

EXAMPLE 46

Example 45 was repeated, with the only exception that pure para-acetylaminotoluene was used instead of a technical grade one: Yield: 89.1% of the theoretical yield. Purity: 96.0%.

EXAMPLE 47

Example 45 was repeated, with the only exception that the methylene chloride and the nitric acid were initially introduced and the para-acetylaminotoluene was added dropwise in the form of a melt. Yield: 89.1% of the theoretical yield. Purity: 98.0%.

EXAMPLE 48

In an experiment similar to that described in Example 45, 600 liters of methylene chloride and 152.25 kg (1000 mols) of a technical grade para-acetylaminotoluene are initially introduced into a one cubic meter vessel, and are heated to the boiling point under normal pressure. It was intended to add dropwise in the course of 3 hours, 154.3 kg (2400 mols) of 98% strength nitric acid. However, the reaction was retarded but started spontaneously after the addition of approximtely one third to one half of the nitric acid. The reaction became violent in such a manner that the experiment had to be interrupted on the grounds of labor safety.

EXAMPLE 49

An experiment was conducted according to Example 45, with the only exception that the melted para-acetylamino toluene and the nitric acid are simultaneously added dropwise. In addition, 0.33 g of 40% NaNO₂ solution are laid before. Yield: 96.3% of the theoretical yield. Purity: 98.8%.

EXAMPLE 50

An experiment according to Example 49 was repeated with the only exception that 10% of the nitric acid was initially introduced with the methylene chloride and only 90% of the nitric acid was simultaneously added with the para-acetylamino toluene. Yield: 95.9% of the theoretical yield. Purity: 98.8%.

EXAMPLE 51

An experiment according to Example 49 was repeated with the only exception that 50% of the nitric acid were initially introduced with the methylene chloride. Only the residual 50% of nitric acid are simultaneously added with the para-acetylamino toluene. Yield: 96.0% of the theoretical yield. Purity: 98.5%.

EXAMPLE 52

An experiment according to Example 50 was conducted with the exception that a one cubic meter vessel was used. Thus, 600 l of methylene chloride, 15.45 kg of 98% strength nitric acid and 0.169 kg 40% aqueous $NaNO_2$ solution are initially introduced into the one cubic meter vessel and are heated to the boiling point under normal pressure. 138.85 kg of 98% strength nitric acid and 152.25 kg technical grade para-acetylamino toluene in the form of a melt are simultaneously added dropwise in the course of 3 hours. Working-up was carried out similar to that described in Example 45 with the only exception that the amounts of water and NaOH are multiplied by a factor of 500. Yield: 95.0% of the theoretical yield: Purity 98.1%.

Table I below summarizes the obtained yields and purities for Examples 45 to 52.

TABLE I

| Example | Reaction Vessel | Order of Addition | Yield % | Purity % |
|---|---|---|---|---|
| 45 | 2 liter flask | successively | 89.1 | 94.85 |
| 46 | 2 liter flask | successively | 89.1 | 96.0 |
| 47 | 2 liter flask | successively | 89.1 | 98.0 |
| 48 | 1 m³ vessel | successively | interrupted | |
| 49 | 2 liter flask | simultaneously | 96.3 | 98.8 |
| 50 | 2 liter flask | simultaneously (90% $HNO_3$) | 95.9 | 98.8 |
| 51 | 2 liter flask | simultaneously (50% $HNO_3$) | 96.0 | 98.5 |
| 52 | 1 m³ vessel | simultaneously (90% $HNO_3$) | 95.0 | 98.1 |

From Table I it is evident that not only the yields and purities of Examples 49 to 51 (simultaneous addition) are superior to those of Examples 45 to 47 (successive addition), but that according to Example 52 in comparison with Example 48 the inventive reaction can be carried out on a commercial scale only if the para-acetylamino toluene and the nitric acid are added simultaneously.

EXAMPLES 53–63

Examples 53 to 63 show that the reaction medium of Karrer et al, "Helvetica Chimica Acta" 19, 1036, (1936), hereinafter the "Karrer citation" or "Karrer", is not comparable in any way with one of the reaction media of the present invention. These examples further show the criticality of the simultaneous addition of the aminotoluene (substrate) and the nitric acid.

Examples 53 to 63 compare sulfuric acid and methylene chloride as reaction media. Examples 53 to 63 were all carried out with 82.6 g (0.5 mols) of 4-tolylcarbamic acid methyl ester. The reaction temperature was held within the range of from −8° C. to −3° C. in order to compare with the Karrer citation. Some of the previous examples herein were carried out at a slightly higher temperature, thus resulting in higher yields. The molar ratios of the substrate to $H_2SO_4$ and $HNO_3$, the respective concentrations and the manner of addition are summarized in Table II hereinbelow. Examples 53 to 63 were all carried out with an additional stirring time of 15 minutes at 0° C. The raw nitrated substrate was noted with respect to its amount and its fusion point. Thereafter this raw nitrated substrate was saponified with approximately 20% by weight NaOH at a molar ratio substrate/NaOH=1:2.8 at reaction conditions of 3 hours at 95° C.

The $HNO_3$ and the $H_2SO_4$ are introduced before the solid substrate is added. After an additional stirring time of 15 minutes, the nitration mixture is poured on 500 g of water and 500 g of ice and the yellow precipitate is filtered off by suction and washed with water until free of acid and dried in vacuo at a temperature of 60° C. The raw nitrated substrate showed a great fusion point interval thus indicating low purity which explains the later found low yield.

Example 54 is generally a repetition of Example 53 with the exception of the grams of 3-$NO_2$-4-$NH_2$-toluene and raw —$NO_2$ substrate are different.

In Experiment 55 the Karrer reaction medium was used, however with the exception that the substrate and the nitric acid were added in a simultaneous manner according to the present invention. The heat of reaction and the additional mixing heat required cooling and thus a reaction time of 150 minutes. The results are summarized in Table II. The raw nitration product also showed a fusion point interval of 12° C.

In Example 56, Example 55 was generally repeated with small variations in grams of raw —$NO_2$ substrate and 3-$NO_2$-4-$NH_2$-toluene.

In Example 57, a reaction medium similar to Karrer was used. The dilution water of the 69.5% strength $HNO_3$ was added mostly to the sulfuric acid (previously cooled). A 98% strength $HNO_3$ was used for simultaneous addition with the substrate. The results as shown in Table II for Example 57 are somewhat better than the results for Examples 53 to 56, however. These examples do not reach the results of some of the previous examples herein.

In Example 58, Example 57 was generally repeated with some small changes in grams of raw —$NO_2$ substrate and 3-$NO_2$-4-$NH_2$-toluene.

In a planned experiment only a part of the 100% strength $H_2SO_4$ was intended to be introduced before the substrate and the 69.5% $HNO_3$. The substrate dissolved in the remaining $H_2SO_4$ was intended to be added simultaneously. This experiment could not be carried out as the solubility of the substrate in $H_2SO_4$ is not sufficient to give a solution. This experiment is not recorded in Table II.

In a further series of Examples, namely Examples 59 to 63, Examples 60 and 61 being similar to Example 59 and Example 63 being similar to Example 62, $CH_2Cl_2$ was used as the reaction medium. In Examples 59 to 61, the reaction temperature and also the amount of $HNO_3$ as in the Karrer citation were applied. In Examples 62 and 63 the Karrer temperature was applied, however, the amount of $CH_2Cl_2$ and the amount and the concentration of $HNO_3$ were varied. The results of Examples 59 to 61 are recorded in Table II hereinbelow. The raw nitration product shows small fusion point ranges indicating higher purities.

EXAMPLES 64 TO 67

The criticality of the simultaneous addition of a substrate and the $HNO_3$ is further shown in Examples 64 to 67.

Example 64 is similar to Example 19 and showed the realization of the desired product in a yield of 94.9% at a purity of 99.8%. Example 65 represents the same example as Example 64, with simultaneous metering of the reactants at the same molar ratio as Example 64, but with a reaction time of 3 hours. In Example 65, the yield dropped slightly to 90.6% at a purity of 99.4%. This is due to the sensitivity of the urethane protective group and the occurrence of some side reactions over a long reaction time. In Example 66, the 4-tolylcarbamic acid ester was introduced in a reaction vessel and thereafter nitric acid was added with the same molar ratio as Example 65, a yield of 90.1% is obtained with a purity of 99.4% when the test was conducted over a period of 1 hour. A yield of only 85.3% at a purity of 99.3% was obtained when the reaction was carried out for 3 hours (Example 67), such 3 hour reaction time is more realistic for a commercial scale, than 1 hour. All data of Examples 64 to 67 are summarized in Table III hereinbelow. It is noted that in Examples 66 and 67, after addition of the half amount of $HNO_3$, the reaction suddenly started and that even at a good external cooling the inner temperature increased to 35° C. It is assumed that with even greater charges this kind of subsequent addition of substrate and $HNO_3$ would be no longer operable from a standpoint of labor safety.

What is claimed is:

1. In a process for the preparation of a nitroaminobenzene by nitrating with nitric acid an aminobenzene which is protected at the nitrogen by a protective group, the improvement which comprises simultaneously introducing 30% to 99% by weight of the total amount of the nitric acid and said aminobenzene to be nitrated into a reaction vessel containing 1% to 70% by weight of the total amount of the nitric acid, and one or more inert solvents and/or diluents, and splitting off the protective group of the nitroaminobenzene after the nitroaminobenzene is prepared.

2. A process according to claim 1, wherein said inert solvent and/or diluent is methylene chloride.

3. A process according to claim 1, wherein the nitration is conducted at a temperature of between about 0° C. and about 80° C.

4. A process according to claim 3, wherein said aminobenzene is p-acetylaminotoluene.

5. A process according to claim 4, wherein the nitration is conducted using a concentration of nitric acid of 60 to 100% by weight.

6. A process according to claim 5, wherein 2 to 6 mols of 100% strength by weight nitric acid is employed per mol of p-acetylaminotoluene.

7. A process according to claim 6, wherein the nitration is conducted in the absence of sulfuric acid.

8. A process according to claim 5, wherein the inert solvent and/or diluent contains some of the nitric acid required for the nitration.

TABLE II

NITRATION OF 4-TOLYLCARBAMIC ACID METHYL ESTER

| Example Nos. | $CH_2Cl_2$ ml | $H_2SO_4$ mols | $H_2SO_4$ conc. | $HNO_3$ 69.5% mols | Added $HNO_3$ mols | Added $HNO_3$ conc. | substrate | Time min. | raw $NO_2$- substrate g | raw $NO_2$- substrate Fp. °C. | 3-$NO_2$—4-$NH_2$ toluene g | 3-$NO_2$—4-$NH_2$ toluene yield | 3-$NO_2$—4-$NH_2$ toluene purity | Addition of $HNO_3$ |
|---|---|---|---|---|---|---|---|---|---|---|---|---|---|---|
| 53 | — | 1.715 | 100% | 3.97 | — | — | as a solid | 60 | 87.02 | 87–97 | 39.92 | 48.4% | 92.2% | not simultane |
| 54 | — | 1.715 | 100% | 3.97 | — | — | as a solid | 60 | 87.69 | 87–97 | 40.91 | 49.5% | 92.0% | not simultane |
| 55 | — | 1.715 | 100% | — | 3.97 | 69.5% | as a solid | 150 | 83.85 | 86–98 | 33.85 | 40.3% | 90.6% | simultaneous |
| 56 | — | 1.715 | 100% | — | 3.97 | 69.5% | as a solid | 150 | 83.34 | 86–97 | 31.78 | 37.8% | 90.4% | simultaneous |
| 57 | — | 1.715 | 61.6% | — | 3.97 | 98% | as a solid | 105 | 88.88 | 89–99 | 55.28 | 71.3% | 98.1% | simultaneous |
| 58 | — | 1.715 | 61.6% | — | 3.97 | 98% | as a solid | 105 | 89.96 | 90–97.5 | 55.73 | 72.4% | 98.8% | simultaneous |
| 59 | 85 | — | — | — | 3.97 | 69.5% | dissolved in 240 ml $CH_2Cl_2$ | 70 | 95.85 | 99.5–101 | 69.10 | 90.5% | 99.7% | simultaneous |
| 60 | 85 | — | — | — | 3.97 | 69.5% | dissolved in 240 ml $CH_2Cl_2$ | 70 | 95.47 | 101–102 | 68.30 | 89.4% | 99.6% | simultaneous |
| 61 | 85 | — | — | — | 3.97 | 69.5 | dissolved in 240 ml $CH_2Cl_2$ | 70 | 97.60 | 100–101 | 68.57 | 89.9% | 99.8% | simultaneous |
| 62 | 50 | — | — | — | 1.0 | 98% | dissolved in 240 ml $CH_2Cl_2$ | 70 | 99.18 | 99–101 | 69.70 | 91.4% | 99.8% | simultaneous |
| 63 | 50 | — | — | — | 1.0 | 98% | dissolved in 240 ml $CH_2Cl_2$ | 70 | 98.25 | 99–101 | 69.56 | 91.3% | 99.9% | simultaneous |

TABLE III

NITRATION OF 4-TOLYLCARBAMIC ACID METHYL ESTER (1 mol) WITH 98% STRENGTH $HNO_3$ (1.7 mol) at 20° C.
THE TOTAL AMOUNT OF $CH_2Cl_2$ is 650 ml IN ALL EXAMPLES 64–67

| Example Nos. | LAID BEFORE $CH_2Cl_2$ ml | LAID BEFORE SUBSTRATE mol | Added $HNO_3$ mol | Added SUBSTRATE mol | $CH_2Cl_2$ mol | TIME MIN | 3-$NO_2$—4-$NH_2$—TOLUENE g | 3-$NO_2$—4-$NH_2$—TOLUENE yield | 3-$NO_2$—4-$NH_2$—TOLUENE purity |
|---|---|---|---|---|---|---|---|---|---|
| 64 | 100 | — | 1.7 | 1 | 550 | 60 | 144.7 | 94.9% | 99.8% |
| 65 | 100 | — | 1.7 | 1 | 550 | 180 | 138.7 | 90.6% | 99.4% |
| 66 | 500 | 1 | 1.7 | — | 150 | 60 | 137.9 | 90.1% | 99.4% |
| 67 | 500 | 1 | 1.7 | — | 150 | 180 | 130.8 | 85.3 | 99.3% |

9. A process according to claim 4, wherein the inert solvent and/or diluent contains nitrous acids and/or salts thereof and/or anhydrides thereof and/or nitrosyl sulfuric acid.

10. A process according to claim 1, wherein said aminobenzene is 4-tolylcarbamic acid ester.

11. A process according to claim 10, wherein the nitration is carried out at a temperature of −10° C. to +45° C.

12. A process according to claim 11, wherein the nitric acid is of the strength of 50 to 100% by weight.

13. A process according to claim 12, wherein the 4-tolylcarbamic ester has the formula

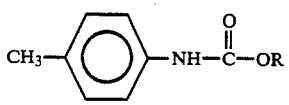

wherein
R represents a cycloaliphatic or aliphatic radical with 1 to 8 carbon atoms.

14. A process according to claim 1, wherein the concentration of the nitric acid is between about 50% and about 100% strength by weight.

15. A process according to claim 1, wherein said aminobenezene is of the general formula

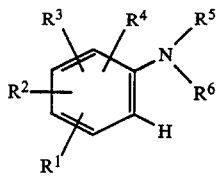

wherein
$R^1$ to $R^4$ are identical or different and represent 1 to 4 hydrogen atoms, 1 to 4 halogen atoms, 1 to 4 alkyl radicals, 1 to 2 alkoxy radicals, 1 to 2 acyloxy radicals, 1 to 2 aryloxy radicals, an acylamino radical, a carboxyl radical, an alkoxycarbonyl radical, an alkylsulphonyl radical, an aralkoxy radical, an aralkylsulphonyl radical, an arylsulphonyl radical, a hydroxysulphonyl radical or an aminosulphonyl radical,
$R^5$ denotes hydrogen and
$R^6$ denotes formyl, oxalyl, alkylcarbonyl, alkylsulphonyl, arylcarbonyl, arylsulphonyl, the group CO—OR, wherein R represents a cycloaliphatic or an aliphatic radical of 1 to 8 carbon atoms, or

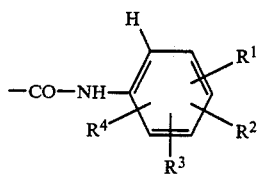

wherein
$R^1$ to $R^4$ have the abovementioned meaning, or
$R^6$ denotes

—CO—NH—R' wherein

R' is hydrogen or alkyl, or
$R^5$ and $R^6$ together represent a phthalyl radical or
$R^5$ and $R^6$ conjointly with a ring carbon atom which is in the ortho-position to the carbon atom substituted by the protected amino group form a 2-methyl-substituted oxazole ring, an oxazolone ring or a 2,6-dioxo-dihydro-1,3-oxazine ring, in which case, at the same time, one of the radicals $R^1$ to $R^4$ other than hydrogen must be present in the para-position to the ring carbon atom which is substituted by the protected amino group.

16. A process according to claim 1, wherein said aminobenzene is of the general formula

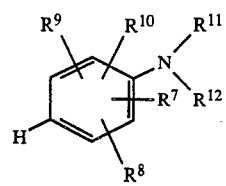

$R^7$ to $R^{10}$ are identical or different and represent 1 to 4 hydrogen atoms, 1 to 4 halogen atoms, 1 to 4 alkyl radicals, 1 to 2 alkoxy radicals, 1 to 2 acyloxy radicals, 1 to 2 aryloxy radicals, an acylamino radical, a carboxyl radical, an alkoxycarbonyl radical, an alkylsulphonyl radical, an aralkoxy radical, an aralkylsulphonyl radical, an arylsulphonyl radical, a hydroxysulphonyl radical or an aminosulphonyl radical,
$R^{11}$ denotes hydrogen and
$R^{12}$ denotes formyl, oxalkyl, alkylcarbonyl, alkylsulphonyl, alkoxycarbonyl, arylcarbonyl, arylsulphonyl or

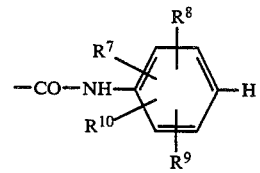

wherein
$R^7$ to $R^{10}$ are identical or different and have the abovementioned meaning, or
$R^{12}$ denotes

—CO—NH—R' wherein
R' represents hydrogen or alkyl, or
$R^{11}$ and $R^{12}$ together represent a phthalyl radical or
$R^{11}$ and $R^{12}$, conjointly with a ring carbon atom which is in the ortho-position to the carbon atom substituted by the protected amino group form a 2-methyl-substituted oxazole ring, and oxazolone ring or a 2,6-dioxo-dihydro-1,3-oxazine ring.

17. A process according to claim 1, which further comprises conducting the nitration in the presence of nitrous acid.

18. A process according to claim 1, which further comprises conducting the nitration in the presence of water binding agents.

19. A process according to claim 1, wherein said splitting off is conducted after first removing said inert solvent and/or diluent.

20. A process according to claim 1, wherein the protective group of the nitroaminobenzene is split off in an acid medium.

21. A process according to claim 1, characterized in that the protective group of the nitroaminobenzene is split off in an alkaline medium.

22. A process according to claim 1, wherein after completion of nitration excess nitric acid is removed, completely or partially from the nitration mixture, thereafter the protective group of the nitroaminobenzene is split off, and the nitroaminobenzene is subsequently isolated.

23. A process according to claim 22, wherein excess nitric acid is removed, completely or partially from the nitration mixture by means of extraction with water.

24. A process according to claim 1, wherein 1.1 to 9 mols of a 100% strength by weight nitric acid are employed per mol of aminobenzene.

25. A process according to claim 1, wherein 1.3 to 15 mols of a 50% strength by weight nitric acid are employed per mol of aminobenzene.

26. A process according to claim 1, wherein 400 to 2,500 ml of said inert solvent and/or diluent are employed per mol of aminobenzene.

27. A process according to claim 1, wherein said nitration is conducted at a pressure of 0.2 to 3.5 bar.

28. A process for the preparation of 3-nitro-4-aminotoluene which comprises simultaneously combining 4-tolylcarbamic acid ester and 50 to 100% strength by weight nitric acid at a temperature of −10° to +45° C. in the presence of an inert water-immiscible organic solvent and/or diluent and thereafter effecting alkaline saponification and working up of the reaction product, wherein the 4-tolylcarbamic acid ester and 30% to 99% by weight of the total amount of the nitric acid are added simultaneously to a mixture of inert organic solvents and/or diluents and 1% to 70% by weight of the total amount of the nitric acid.

29. A process for the preparation of 3-nitro-4-aminotoluene which comprises:
 (a) contacting 4-tolycarbamic acid ester with 50 to 100% by weight nitric acid at a temperature of −10° to +45° C. in the presence of an inert water-immiscible organic solvent and/or diluent, the nitration mixture including said water-immiscible organic solvent and/or diluent, said 4-tolylcarbamic acid ester, water and said nitric acid, said 4-tolylcarbamic acid ester and said nitric acid being added simultaneously to said inert water-immiscible organic solvent and/or diluent; and
 (b) thereafter effecting alkaline saponification of the resultant nitrated 4-tolylcarbamic acid ester and working up the reaction product by distillation, phase separation, extraction and/or filtration.

30. A process according to claim 29, wherein said 4-tolylcarbamic acid ester has the formula

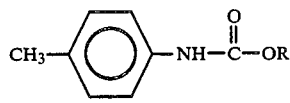

wherein
 R represents a cycloaliphatic or aliphatic radical with 1 to 8 carbon atoms.

31. A process according to claim 30, wherein R represents methyl, ethyl, n-propyl, iso-propyl, n-butyl, iso-butyl, tert.-butyl, n-pentyl, iso-pentyl, n-hexyl or cyclohexyl.

32. A process according to claim 28, wherein 1.5 to 5 mols of 100% strength by weight nitric acid are employed per mol of 4-tolylcarbamic acid ester.

33. A process according to claim 28, wherein 3 to 10 mols of 50% strength by weight nitric acid are employed per mol of 4-tolylcarbamic acid ester.

34. A process according to claim 28, wherein 400 to 2,000 ml of inert organic solvent and/or diluent are employed per mol of 4 tolylcarbamic acid ester.

35. A process according to claim 28, wherein the reaction is carried out at a temperature of 0° to 40° C.

36. A process according to claim 28, wherein the reaction is carried out at temperature of 10° to 25° C.

37. In a process for the preparation of 3-nitro-4-aminotoluene by nitration of p-acetylaminotoluene in the presence of an inert, water-immiscible organic solvent at a temperature in the range of from 0° to 80° C. followed by alkaline saponification of the reaction mixture and recovery of 3-nitro-4-aminotoluene, the improvement wherein the nitration is carried out using nitric acid of 60 to 100% strength by weight in the presence of methylene chloride, 30% to 99% by weight of the total amount of the nitric acid and p-acetylaminotoluene being simultaneously added to said inert water-immiscible organic solvent initially introduced and wherein said methylene chloride initially introduced contains 1% to 70% by weight of the total amount of the nitric acid required for the nitration.

38. A process according to claim 37, wherein 2 to 6 mols of 100% strength by weight nitric acid are employed per mol of p-acetylaminotoluene.

39. A process according to claim 37, wherein 6 to 12 mols of 60% strength by weight nitric acid are employed per mol of p-acetylaminotoluene.

40. A process according to claim 37, wherein 400 to 2,000 ml of methylene chloride are employed per mol of p-acetylaminotoluene.

41. A process according to claim 37, wherein the reaction of p-acetylaminotoluene and nitric acid are effected in the absence of sulfuric acid.

42. A process according to claim 37, wherein said methylene chloride initially introduced contains nitrous acid and/or salts thereof and/or anhydrides thereof and/or nitrosyl sulfuric acid.

43. A process according to claim 1, wherein said aminobenzene has the formula

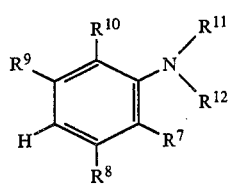

wherein
 $R^7$ represents hydrogen, halogen, alkyl, alkoxy, acyloxy, acylamino, carboxyl, alkyl, arylsulphonyl or aryloxy,
 $R^8$ represents hydrogen, halogen, alkyl, alkoxy, alkoxycarbonyl, acyloxy, acylamino, carboxyl, alkylsulphonyl or arylsulphonyl,
 $R^9$ represents hydrogen, halogen, alkyl, alkoxy, alkoxycarbonyl, acyloxy, acylamino, alkylsulphonyl, arylsulphonyl or aralkylsulphonyl, $R^{10}$ represents hydrogen, halogen or alkyl,
$R^{11}$ denotes hydrogen and
$R^{12}$ denotes formyl, oxalyl, alkylcarbonyl, alkylsulphonyl, alkoxycarbonyl, arylcarbonyl, acylsulphonyl or

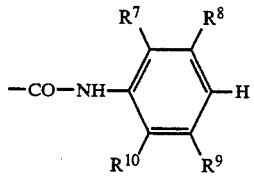

wherein
$R^7$ to $R^{10}$ are identical or different and have the previously mentioned meanings, or $R^{12}$ represents

—CO—NH—R' wherein
R' represents hydrogen or alkyl, or
$R^{11}$ $R^{12}$ together represent a phthalyl radical or
$R^{11}$ or $R^{12}$ conjointly with a ring carbon atom which is in the ortho-position to the carbon atom substituted by the protected amino group form a 2-methyl-substituted oxazole ring, and oxazolone ring or a 2,6-dioxo-dihydro-1,3-oxazine ring.

44. A process according to claim 15, wherein said aminobenzene has the formula

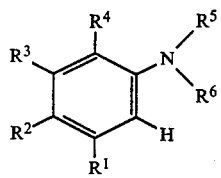

wherein
$R^1$ represents hydrogen, halogen, alkyl or alkoxy;
$R^2$ represents hydrogen, halogen, alkyl, alkoxy, acyloxy, acylamino, alkylsulphonyl, arylsulphonyl, aryloxy, carboxyl or hydroxysulphonyl;
$R^3$ represents hydrogen, halogen, alkyl, alkoxy, acyloxy or acylamino;
$R^4$ represents hydrogen, halogen, alkyl, alkoxy, aryloxy or carboxyl;
$R^5$ denotes hydrogen and
$R^6$ represents formyl, oxalyl, alkylcarbonyl, alkylsulphonyl, alkoxycarbonyl, arylcarbonyl, arylsulphonyl or

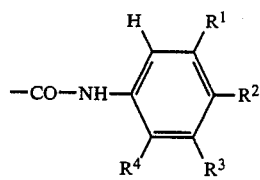

wherein
$R^1$ to $R^4$ are identical or different and have the previously mentioned meanings, or $R^6$ represents

—CO—NH—R' wherein
R' is hydrogen or alkyl, and
$R^6$ represents alkylcarbonyl, alkylsulphonyl, alkoxycarbonyl, arylcarbonyl or arylsulphonyl, or
$R^5$ and $R^6$ together represent a phthalyl radical or $R^5$ and $R^6$ conjointly with a ring carbon atom which is in the ortho-position to the carbon atom substituted by the protected amino group form a 2-methyl-substituted oxazole ring, or an oxazolone ring or a 2,6-dioxo-dihydro-1,3-oxazine ring, in which case, at the same time, one of the radicals $R^1$ to $R^4$ other than hydrogen are present in the para-position to the ring carbon atom which is substituted by the protected amino group.

45. A process according to claim 1, wherein said inert solvent and/or diluent contain from 2% to 50% by weight of the total amount of the nitric acid.

46. A process according to claim 1, wherein said inert solvent and/or diluent contain form 5% to 40% by weight of the total amount of nitric acid.

47. A process according to claim 1, wherein the nitration is conducted at a temperature of between about 0° C. and 80° C., wherein the nitric acid is between about 50% and about 100% strength by weight.

* * * * *